(12) United States Patent
Montero et al.

(10) Patent No.: US 11,819,026 B2
(45) Date of Patent: Nov. 21, 2023

(54) HIGHLY CONCENTRATED BACTERIAL LIQUID SOYBEAN INOCULANT

(71) Applicant: Rizobacter Argentina S.A., Pergamino Buenos Aires (AR)

(72) Inventors: Fabio Montero, Pergamino (AR); Wilter Canciani, Pergamino (AR)

(73) Assignee: RIZOBACTER ARGENTINA S.A., Pergamino Buenos Aires (AR)

( * ) Notice: Subject to any disclaimer, the term of this patent is extended or adjusted under 35 U.S.C. 154(b) by 519 days.

(21) Appl. No.: 16/875,558

(22) Filed: May 15, 2020

(65) Prior Publication Data
US 2021/0352910 A1 Nov. 18, 2021

(51) Int. Cl.
*A01N 63/20* (2020.01)
*C12N 1/20* (2006.01)
*C12N 1/04* (2006.01)

(52) U.S. Cl.
CPC ............... *A01N 63/20* (2020.01); *C12N 1/04* (2013.01); *C12N 1/20* (2013.01)

(58) Field of Classification Search
None
See application file for complete search history.

(56) References Cited

U.S. PATENT DOCUMENTS

2007/0074451 A1* 4/2007 Pearce ................... C12N 1/04
47/57.6

FOREIGN PATENT DOCUMENTS

WO WO-2017116846 A1 * 7/2017 ............... A01C 1/06
WO WO-2020121219 A1 * 6/2020 ............. A01N 63/20

* cited by examiner

*Primary Examiner* — Michelle F. Paguio Frising
(74) *Attorney, Agent, or Firm* — Crowell & Moring LLP

(57) ABSTRACT

This invention includes the composition of a highly concentrated liquid inoculant (between $10^{10}$ and $10^{11}$ cfu/mL) for soybean crops. The composition is packed and has a shelf life of up to 2 years stored at temperatures of up to 25° C. The inoculant may be applied in low doses onto seeds or in the furrow.

39 Claims, 20 Drawing Sheets

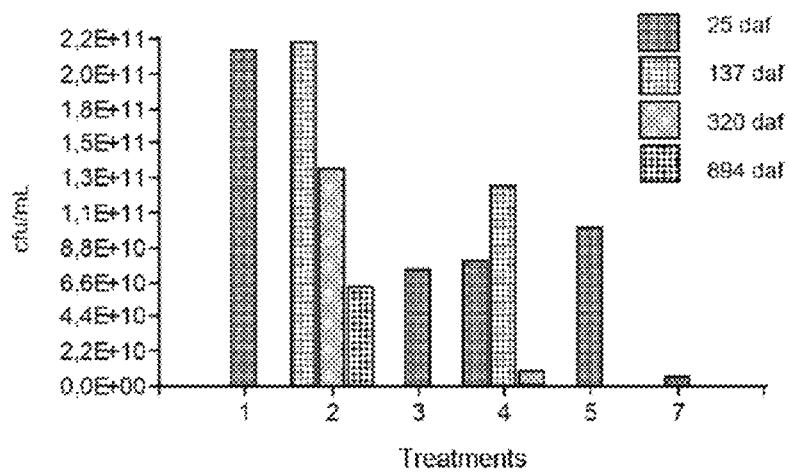

Figure 1

Treatments (inoculants): 1= 8x_A1-30_P2; 2= 8x_A1-30_P4; 3= 8x_A1-60_P2; 4= 8x_A1-60_P4; 5= 8x_A2-30_P2; 7= 8x_A2-60_P2.

8x= concentration of initial bacterial broth; A1= sucrose based stabilizer; A2= trehalose based stabilizer; 30 or 60= percentage of stabilizer in relation to the bacterial broth; P2 or P4= final formulation process of 2 or 4 days.

daf= days after formulation.

cfu/mL= colony forming units of *Bradyrhizobium* per mL of inoculant.

Figure 2

| daf | Inoculant | cfu/mL | pH |
|---|---|---|---|
| 0 | 2 | 1,135E+11 | 8,18 |
|  | 9 | 9,80E+10 | 8,04 |
| 35 | 2 | 1,05E+11 | 7,49 |
|  | 9 | 1,08E+11 | 7,48 |
| 73 | 2 | 1,495E+11 | 7,49 |
|  | 9 | 1,26E+11 | 7,56 |
| 254 | 2 | 9,70E+10 | 7,33 |
|  | 9 | 7,95E+10 | 7,39 |
| 394 | 2 | 4,05E+10 | 7,21 |
|  | 9 | 4,85E+10 | 7,15 |

Inoculant: 2= 8x_A1-30_P4; 9= 8x_A1810-30_P4.

8x= concentration of initial bacterial broth; A1= sucrose based stabilizer; A1810= sucrose and carboxymethyl cellulose based stabilizer; 30= percentage of stabilizer in relation to the bacterial broth; P4= final formulation process of 4 days.

daf= days after formulation.

cfu/mL= colony forming units of *Bradyrhizobium* per mL of inoculant.

Figure 3

| daf | Inoculant | Storage temperature (°C) | cfu/mL | pH |
|---|---|---|---|---|
| 25 | 2 | 16 | 2,65E+11 | 7,24 |
|  | 2 | 20-25 | 1,90E+11 | 7,23 |
| 185 | 2 | 16 | 2,55E+11 | 7,30 |
|  | 2 | 20-25 | 2,10E+11 | 6,90 |
| 255 | 2 | 16 | 6,35E+11 | 7,14 |
|  | 2 | 20-25 | 5,30E+11 | 6,85 |
| 357 | 2 | 16 | 1,80E+11 | 7,25 |
|  | 2 | 20-25 | 9,50E+10 | 7,23 |
| 496 | 2 | 16 | 1,20E+11 | 7,41 |
|  | 2 | 20-25 | 9,50E+10 | 7,28 |
| 720 | 2 | 16 | 5,60E+10 | 6,44 |
|  | 2 | 20-25 | 4,30E+10 | 6,28 |

Inoculant: 2= 8x_A1-30_P4.

8x= concentration of initial bacterial broth; A1= sucrose based stabilizer; 30= percentage of stabilizer in relation to the bacterial broth; P4= final formulation process of 4 days.

daf= days after formulation.

cfu/mL= colony forming units of *Bradyrhizobium* per mL of inoculant.

Figure 4

| daf | Inoculant | cfu/mL | pH |
|---|---|---|---|
| 31 | 2 | 3,60E+11 | 7,72 |
|  | 10 | 3,65E+11 | 7,63 |
|  | 11 | 1,31E+12 | 7,61 |
|  | 12 | 2,45E+11 | 7,75 |
|  | 13 | 3,15E+11 | 7,69 |
|  | 14 | 3,20E+11 | 7,79 |
|  | 15 | 2,15E+11 | 6,11 |
|  | 16 | 2,45E+11 | 7,67 |
|  | 17 | 4,15E+11 | 7,79 |
| 91 | 2 | 1,10E+11 | 7,43 |
|  | 10 | 1,65E+11 | 7,39 |
|  | 11 | 1,86E+11 | 7,43 |
|  | 12 | 1,90E+11 | 7,34 |
|  | 13 | 1,90E+11 | 7,33 |
|  | 14 | 2,12E+11 | 7,32 |
|  | 15 | ND | 5,91 |
|  | 16 | ND | 7,27 |
|  | 17 | 2,65E+11 | 7,45 |
| 209 | 2 | 1,57E+11 | 7,43 |
|  | 10 | 1,99E+11 | 6,79 |
|  | 11 | 2,40E+11 | 7,21 |
|  | 12 | 2,72E+11 | 6,71 |
|  | 13 | 2,72E+11 | 6,93 |
|  | 14 | 2,59E+11 | 6,96 |
|  | 15 | <1,00E+09 | 4,97 |
|  | 16 | 1,31E+11 | 5,26 |
|  | 17 | 2,82E+11 | 6,75 |
| 392 | 2 | 1,10E+11 | 7,45 |
|  | 10 | 1,40E+11 | 5,84 |
|  | 11 | 1,60E+11 | 5,53 |
|  | 12 | 1,20E+11 | 5,32 |
|  | 13 | 5,70E+11 | 7,17 |
|  | 14 | 2,60E+11 | 7,07 |
|  | 15 | <1,00E+09 | 5,09 |
|  | 16 | 1,05E+10 | 4,71 |
|  | 17 | 3,00E+11 | 5,69 |
| 467 | 2 | 1,80E+11 | 7,08 |
|  | 10 | 2,00E+09 | 5,11 |
|  | 11 | <1,00E+09 | 5,10 |
|  | 12 | <1,00E+09 | 5,05 |
|  | 13 | 2,15E+11 | 6,44 |
|  | 14 | 2,55E+11 | 5,82 |
|  | 15 | <1,00E+09 | 5,09 |

Figure 4 continuation

|  |  |  |  |
|---|---|---|---|
|  | 16 | <1,00E+09 | 4,87 |
|  | 17 | 1,60E+11 | 5,27 |
| 542 | 2 | 1,20E+11 | 5,24 |
|  | 10 | <1,00E+09 | 4,88 |
|  | 11 | 1,00E+09 | 4,92 |
|  | 12 | 1,00E+09 | 4,79 |
|  | 13 | 1,45E+11 | 6,73 |
|  | 14 | <1,00E+09 | 5,07 |
|  | 15 | <1,00E+09 | 5,00 |
|  | 16 | <1,00E+09 | 4,82 |
|  | 17 | <1,00E+09 | 5,08 |
| 640 | 2 | 4,17E+10 | 4,63 |
|  | 10 | <1,00E+08 | 4,53 |
|  | 11 | <1,00E+08 | 4,58 |
|  | 12 | <1,00E+08 | 4,46 |
|  | 13 | 4,50E+10 | 4,70 |
|  | 14 | 1,00E+08 | 4,69 |
|  | 15 | <1,00E+08 | 4,66 |
|  | 16 | <1,00E+08 | 4,48 |
|  | 17 | <1,00E+08 | 4,71 |

Inoculant: 2= 8x_A1-30_P4; 10= 10x_A1-37_P4; 11= 10x_A1-30_P4; 12= 13x_A1-50_P4; 13= 13x_A1-40_P4; 14= 13x_A1-30_P4; 15= 20x_A1-75_P4; 16= 20x_A1-50_P4; 17= 20x_A1-30_P4
8x, 10x, 13x or 20x= concentration of initial bacterial broth; A1= sucrose based stabilizer; 30, 37, 40, 50 or 75= percentage of stabilizer in relation to the bacterial broth; P4= final formulation process of 2 or 4 days.
daf= days after formulation.
cfu/mL= colony forming units of *Bradyrhizobium* per mL of inoculant.
ND= Not Determined.

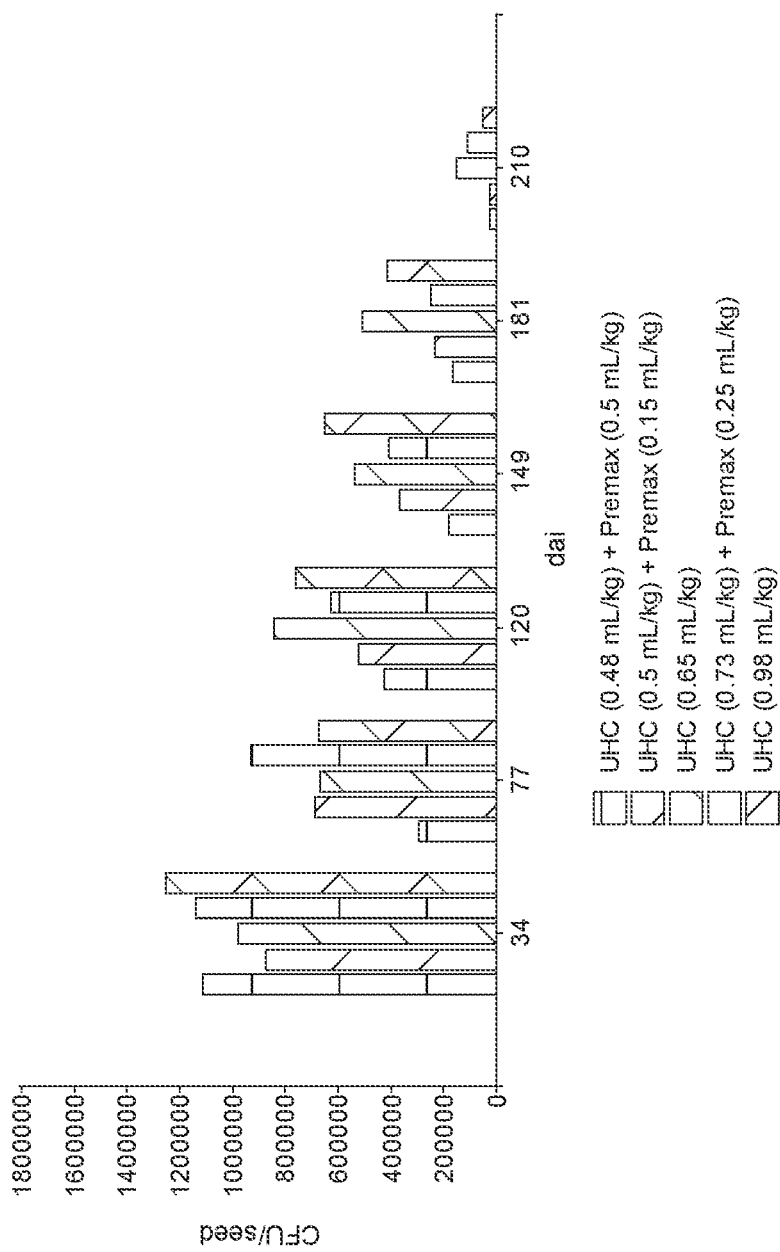
Figure 5 - A

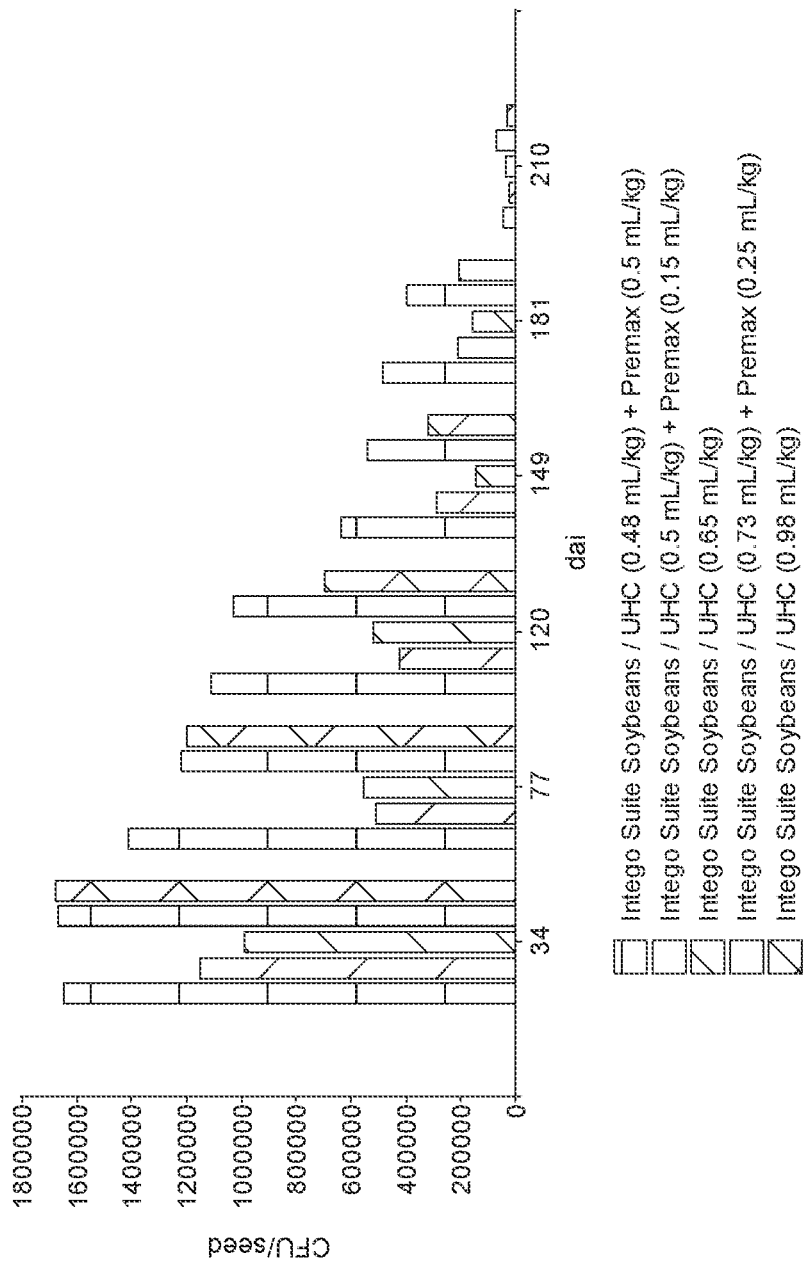
Figure 5 - B

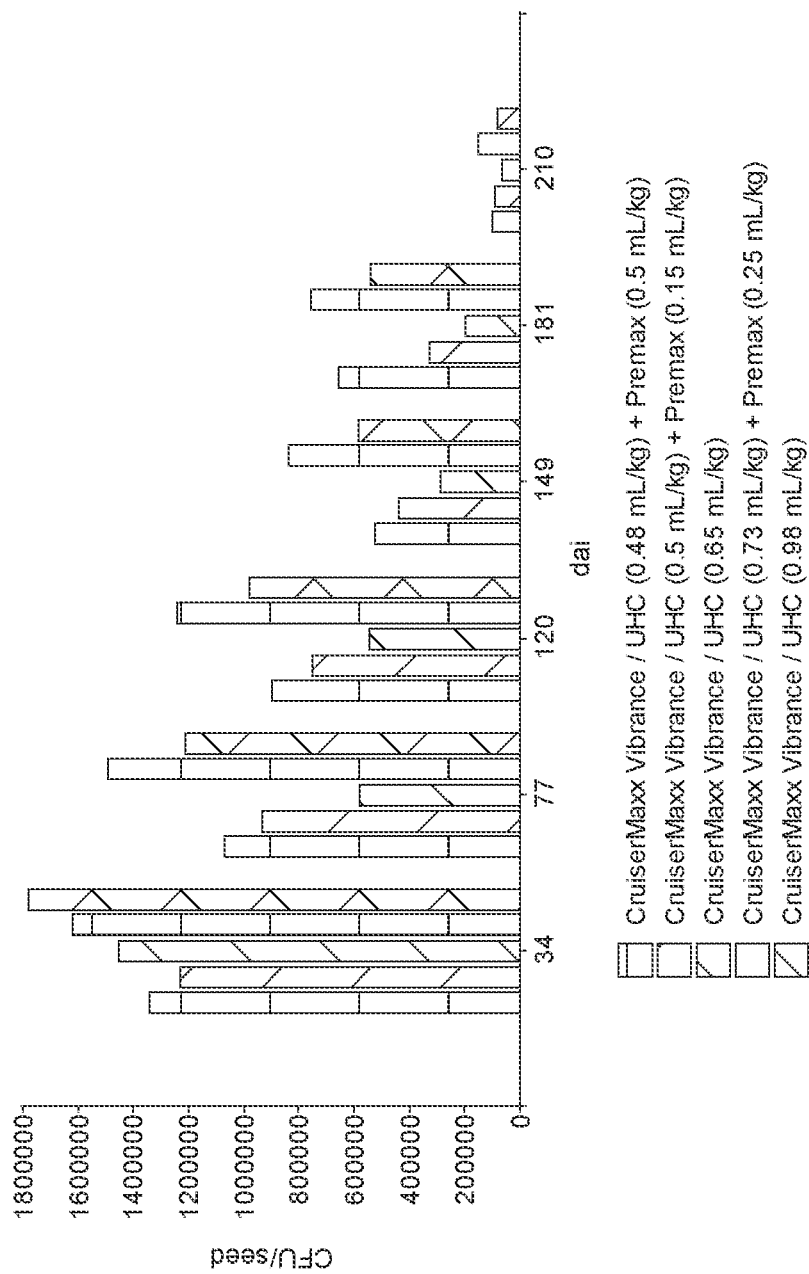
Figure 5 - C

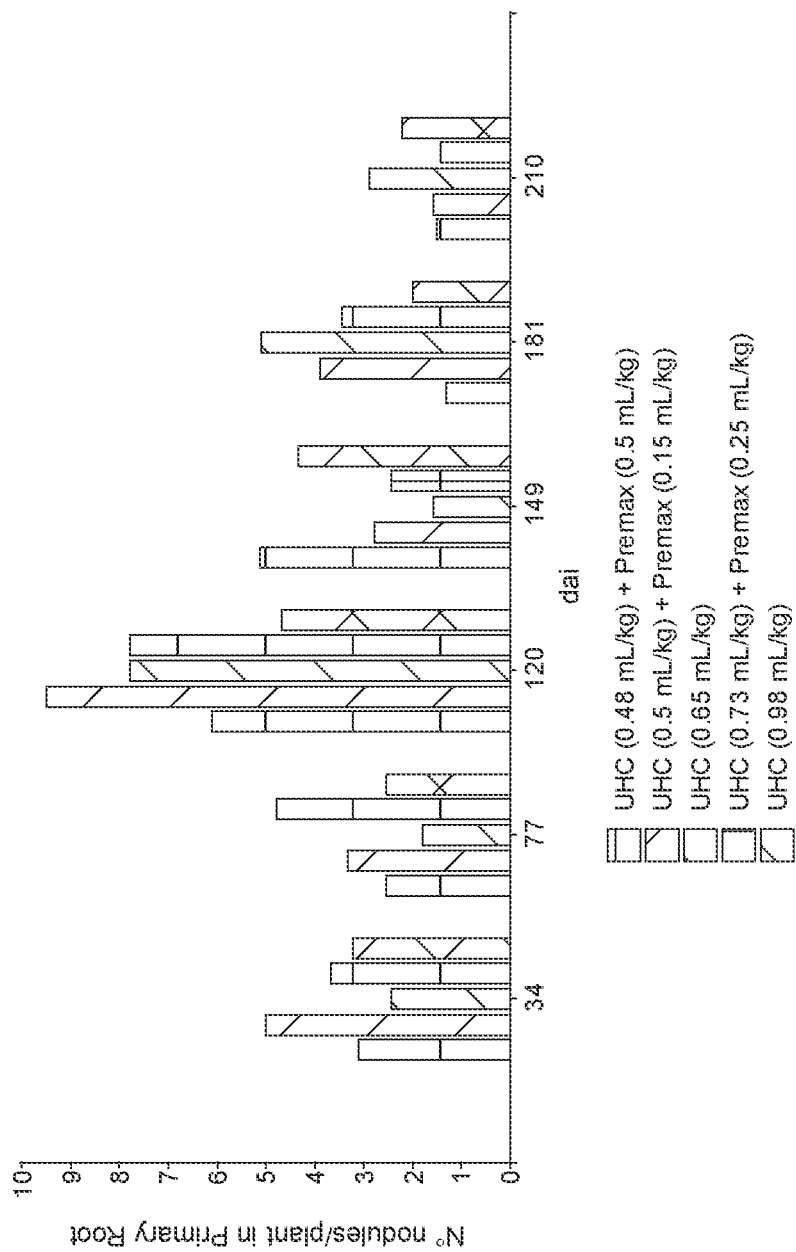
Figure 6 - A

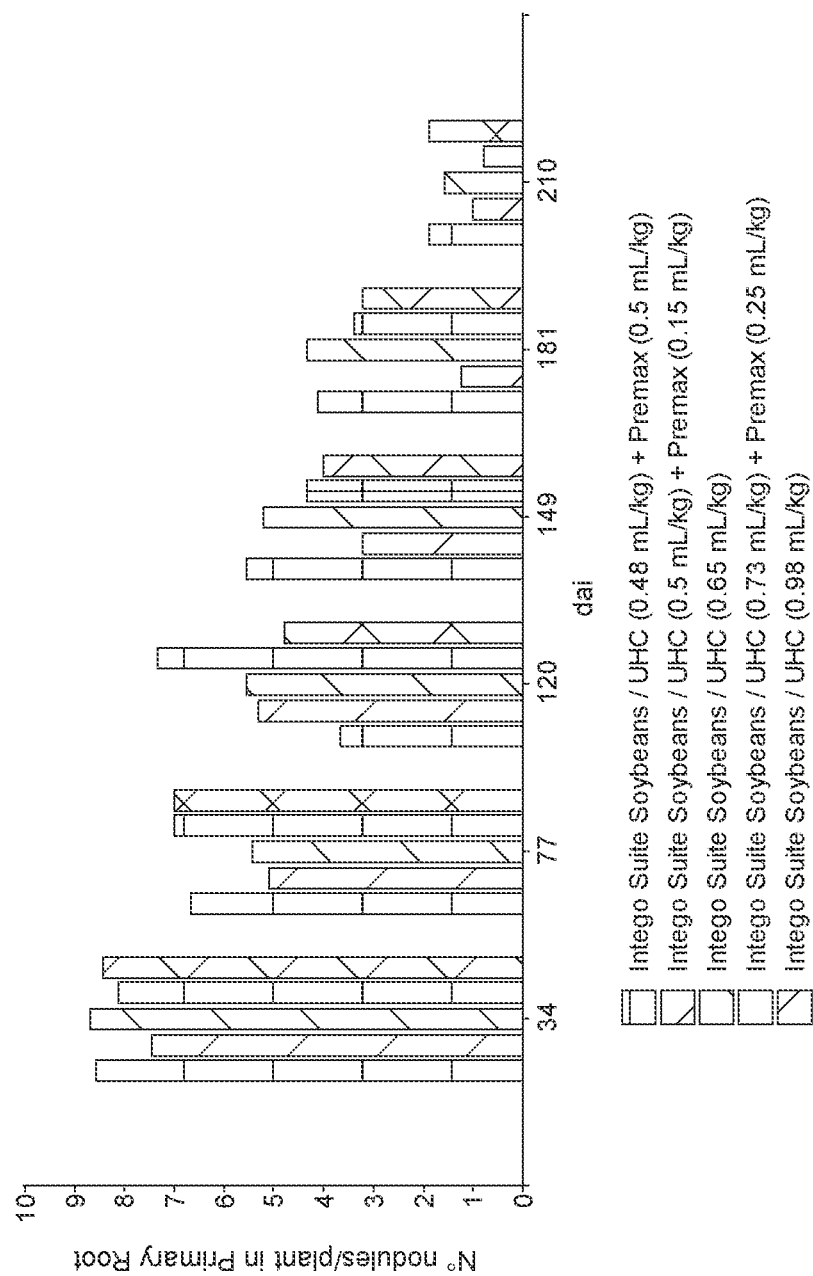
Figure 6 - B

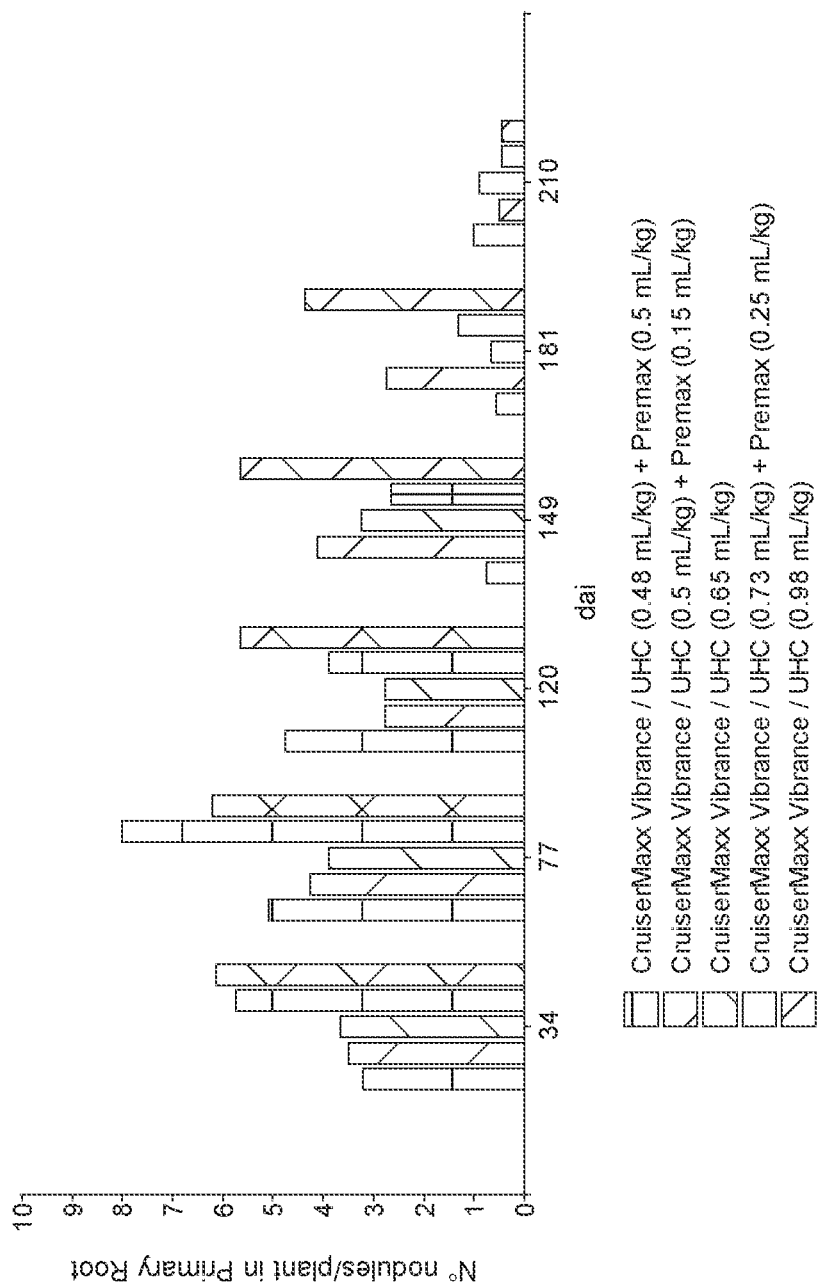
Figure 6 - C

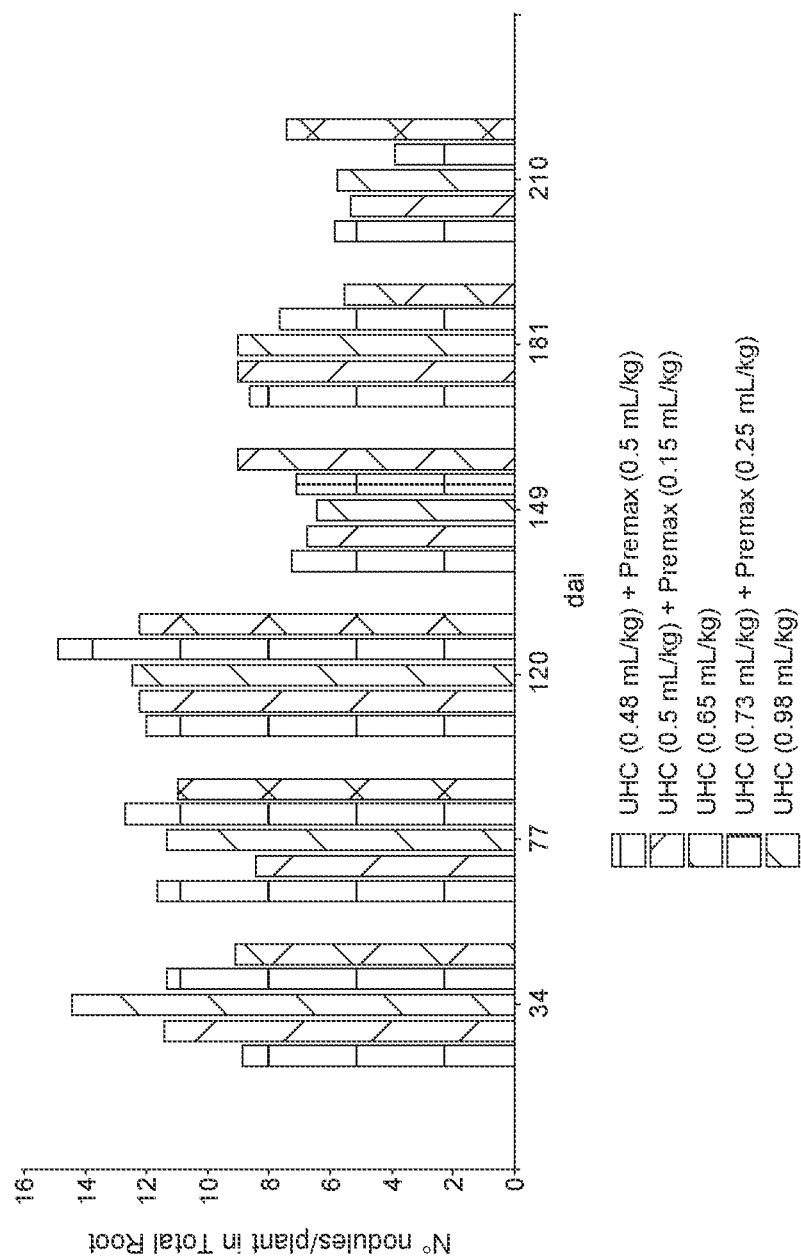
Figure 7 - A

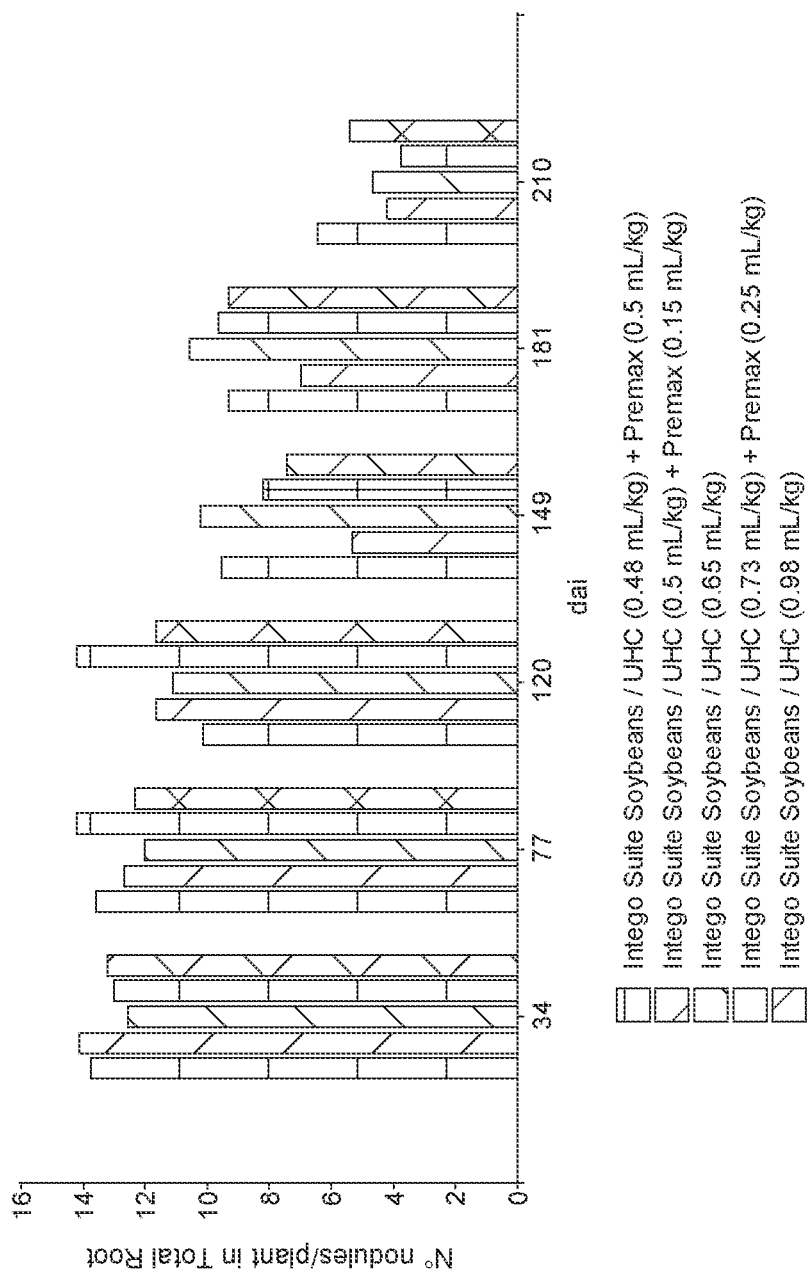
Figure 7 - B

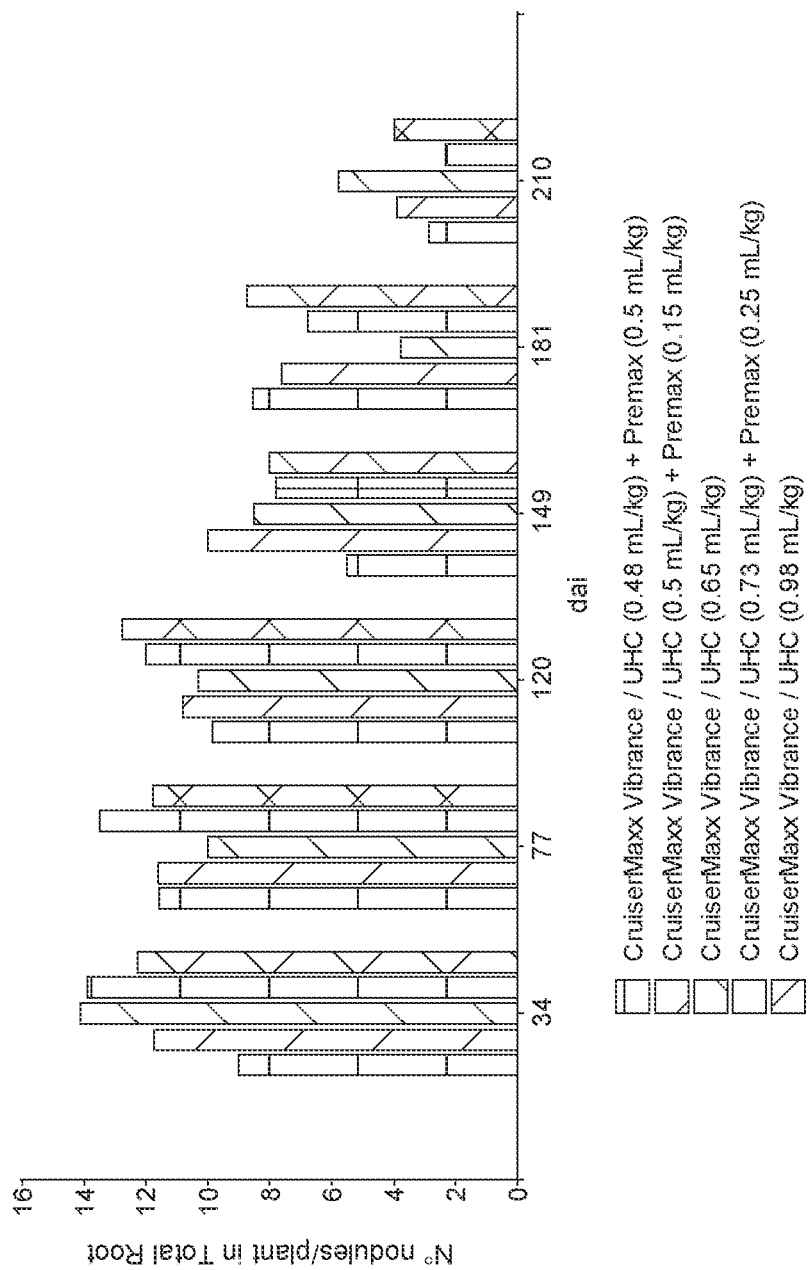
Figure 7 - C

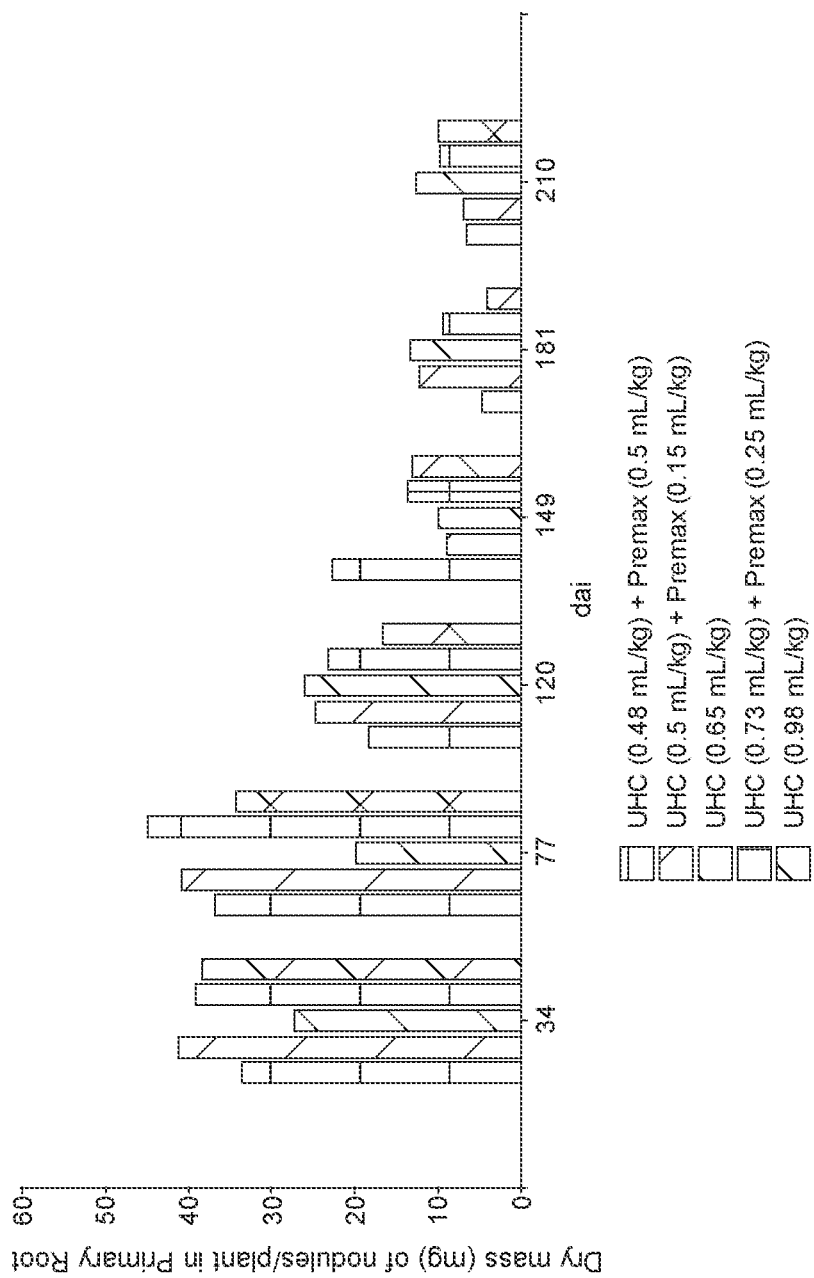
Figure 8 - A

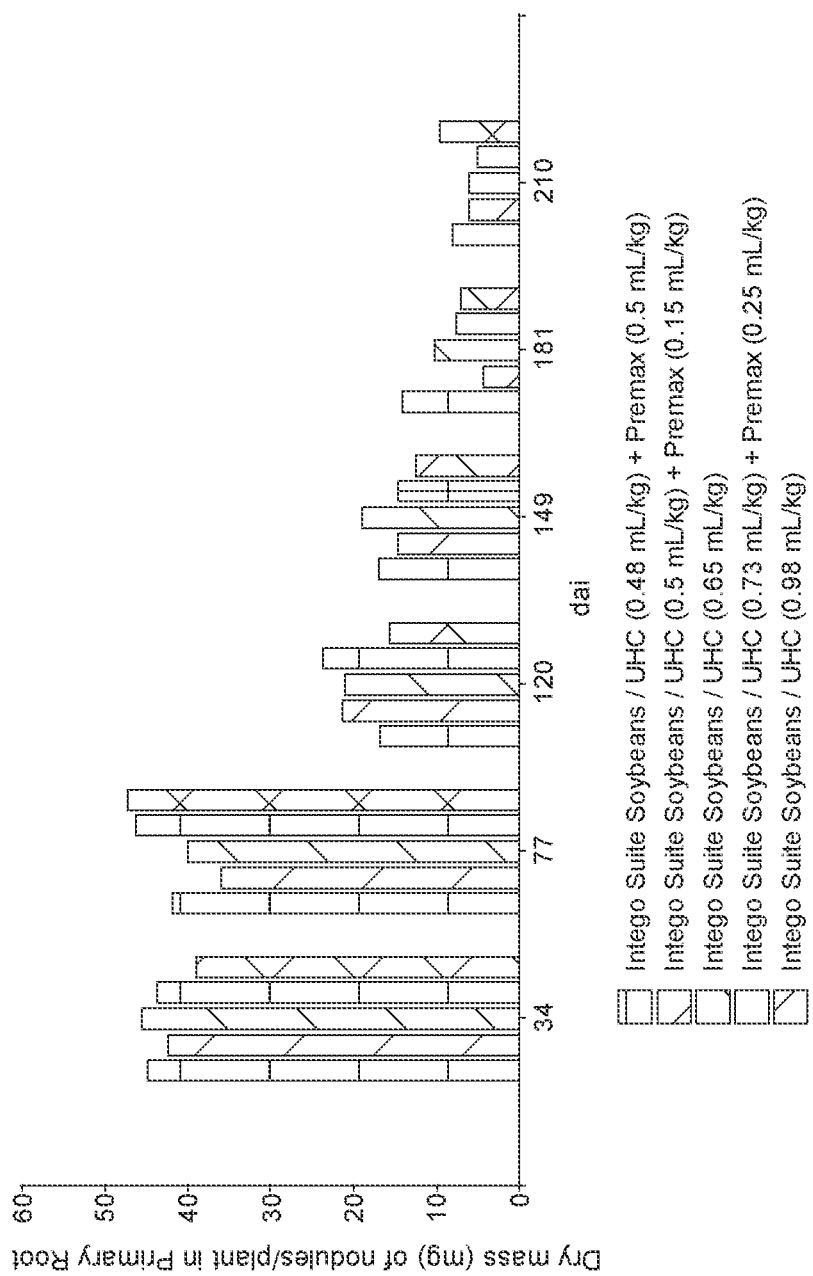
Figure 8 - B

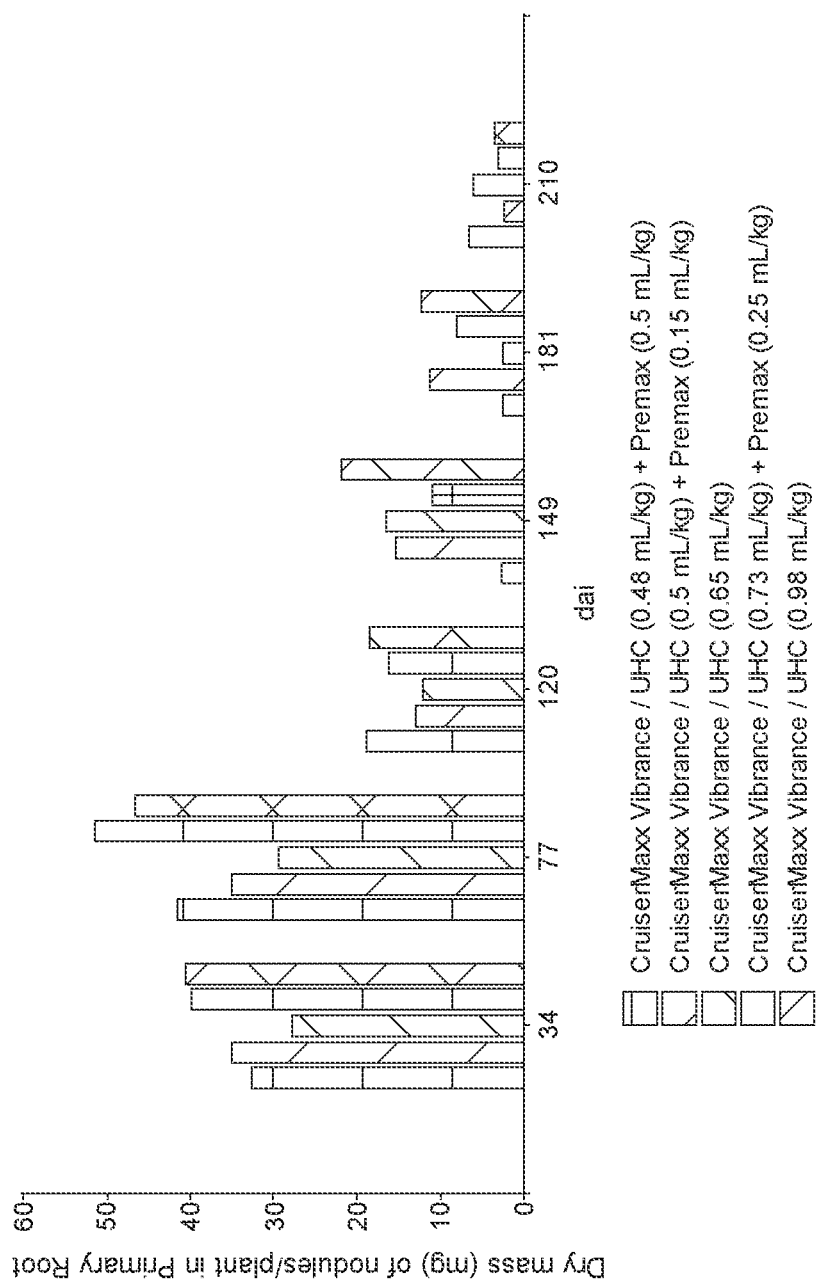
Figure 8 - C

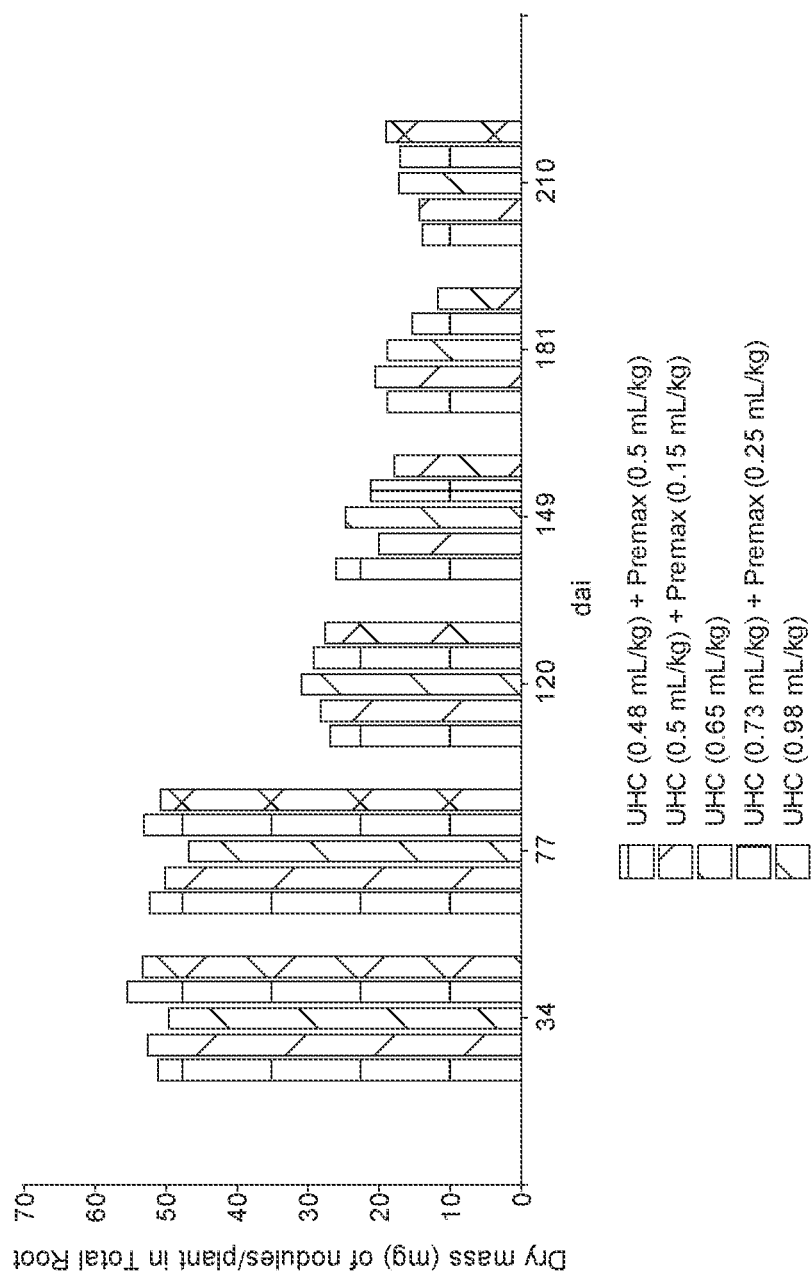
Figure 9 - A

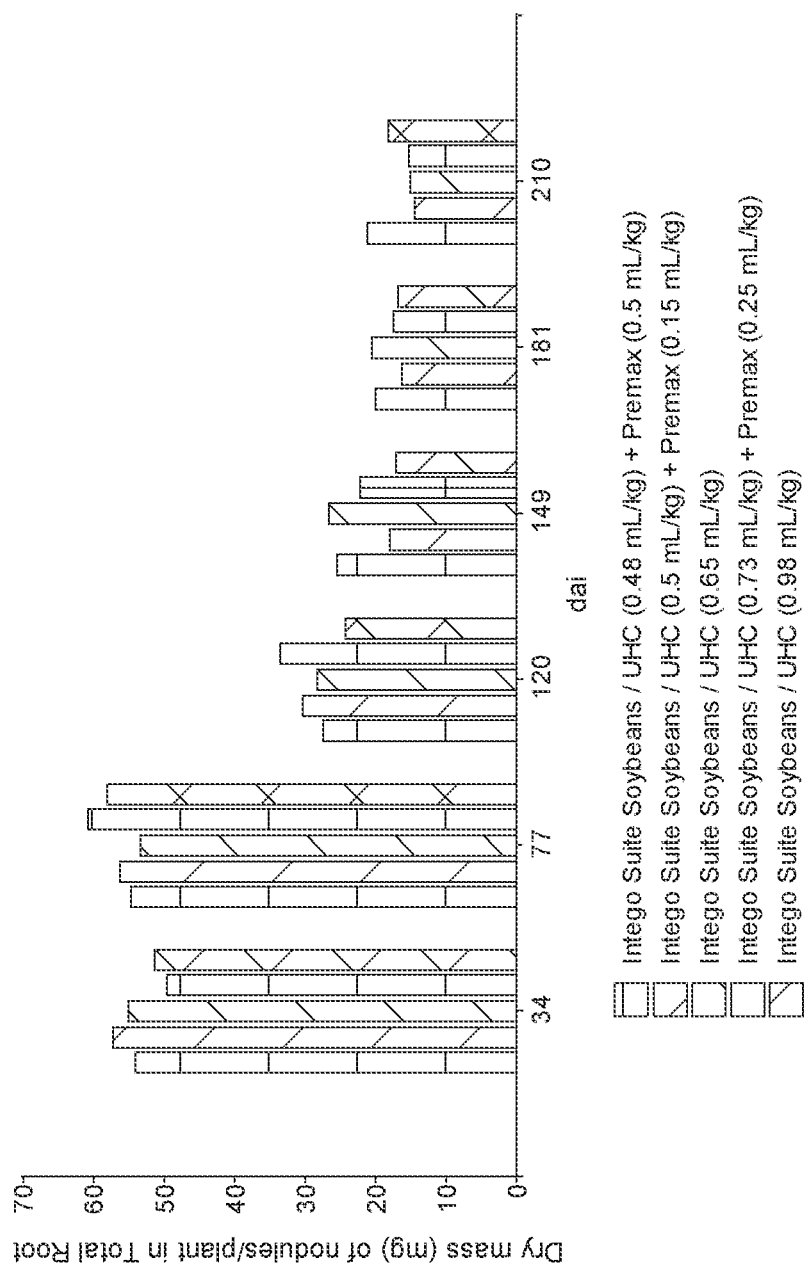
Figure 9 - B

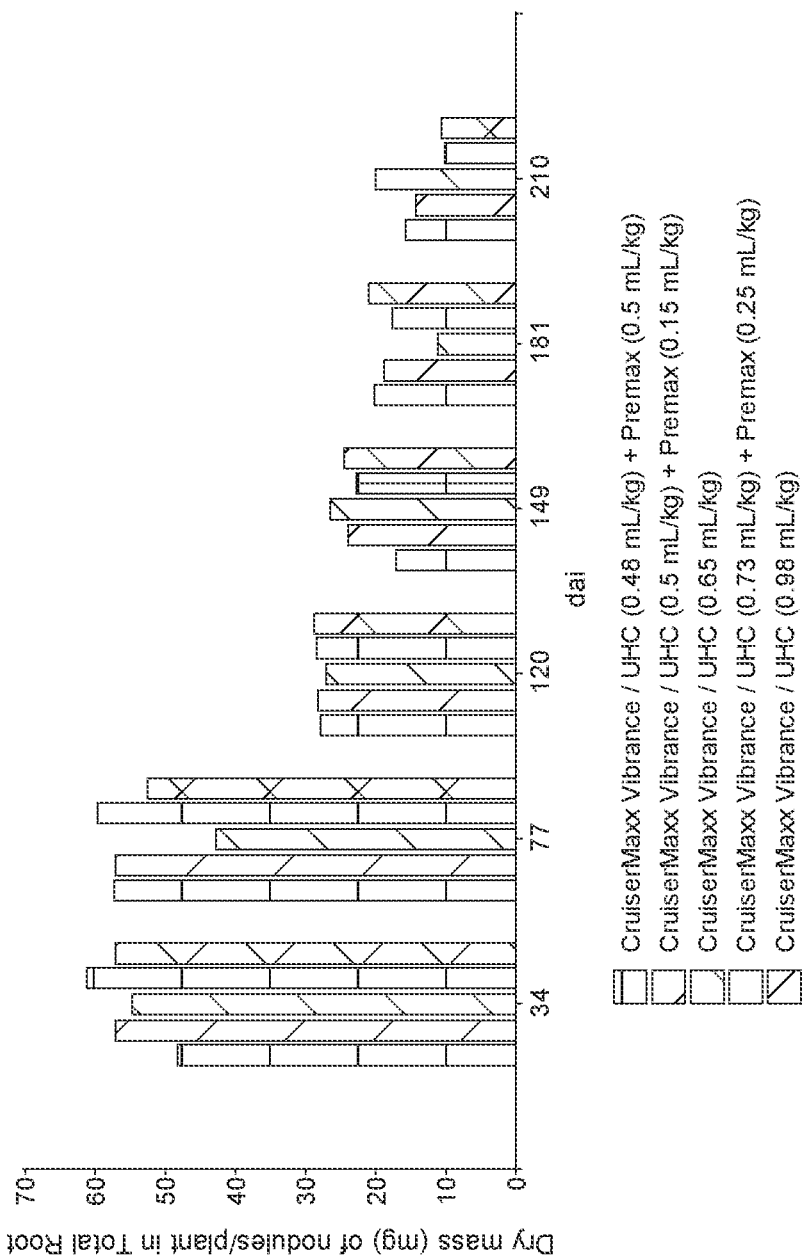
Figure 9 - C

HIGHLY CONCENTRATED BACTERIAL LIQUID SOYBEAN INOCULANT

FIELD OF THE INVENTION

The invention relates to the composition of a liquid inoculant for soybean, which permits a high concentration of bacteria in a container stored at room temperature for up to 2 years, and its application at low doses.

BACKGROUND OF THE INVENTION

Soybean inoculants use bacteria, usually applied to the seeds or to the sowing furrow, to create a symbiosis with the seedling, and thus leverage the use of nitrogen from the air as a nitrogenous nutrient directly provided onto the crop.

The use of inoculants to help the plant transform air nitrogen into usable forms has a strong economic impact on reducing the soybean crop production cost, as the use of more expensive synthetic nitrogen fertilizers is avoided. Moreover, the use of biologically-fixed nitrogen does not have a negative environmental impact, unlike fertilizers with a highly energy-demanding manufacturing process and their application to the crop, which can negatively affect the environment.

The production of commercial soybean inoculants has led to products based on bacteria *Bradyrhizobium japonicum, B. dizoefficiens* or *B. elkanii* contained in different carriers or inerts. These can be of a different nature such as peat or clay based powders, or aqueous or oily liquids. Each provides advantages and disadvantages from the point of view of bacterial stability and ease of use of the product.

The greatest demand for inoculants based on the type of formulation carrier is for liquids, preferably aqueous ones. These types of inoculants provide convenience of application both to the seed and to the sowing furrow and are adapted to many situations and treatment variants.

Commercial liquid inoculants generally have a shelf life of 6 to 18 months and their storage temperature ranges between 5 and 25° C. Storage and transport must occur away from solar radiation.

When treating seeds, the use of an inoculant together with phytosanitary products and other chemical or biological products is very common, since the user needs to ensure the correct establishment of the crop. Products such as fungicides, insecticides, nematicides, micronutrients, polymers, among others, minimize the risk of phytopathogens and insects attack, and provide excellent seed coverage, thus achieving homogeneity of application, proper movement and a good aspect.

However, from the point of view of the seed integrity, there is a limit to the amount of products to be applied onto it, beyond which problems such as deterioration, germination and adhesiveness between seeds may occur. The maximum volume of liquid that can be tolerated by soybean without generating inconveniences is approximately 5 mL/kg for a single simultaneous application and 10 mL/kg for the sum of sequential applications. The seed grower should apply all relevant products without exceeding this volume. It is here when the use the lowest possible doses of products while maintaining their effectiveness to minimize the risks of seed deterioration becomes vital.

The available soybean inoculants on the market are applied at relatively high doses (approximately 2-3 mL/kg) and several of them involve the use of a bacterial protector (approximately 0.5-2 mL/kg) which contributes to increasing the total dose of products intended to leverage nitrogen from the air. These amounts of inoculant and protection plus the other products in a typical seed treatment may exceed the maximum recommended liquid limit and, therefore, increase the risks of failure (biological and/or physical). Furthermore, highly concentrated products may be available in paste form. However, they require refrigerated storage and an activation process before application, which affects their cost and practicality of use. This is why they are generally used as an input for other types of inoculants and not as an end product.

Besides contributing to the efficiency of seed treatment, low doses of inoculant result in a reduction of transportation cost, storage space, energy consumed during application, and general handling. In addition, they result in a positive impact on the environment due to the reduction of the amount of packaging material used per seed weight unit.

Consequently, there is a need for a soybean inoculant composition with a high concentration of bacterial count per volume unit (between $10^{10}$ and $10^{11}$ cfu/mL), which can be stored and transported under normal room temperature conditions for inoculants in general, which maintains its effectiveness over a long shelf life in its packaging, which is liquid in order to maximize its practicality of use, and which is applied at relatively low doses so that it can be applied together with other products.

BRIEF DESCRIPTION OF THE INVENTION

This invention relates to a composition of a liquid inoculant for soybean, with a high concentration of bacteria per volume unit (between $10^{10}$ and $10^{11}$ cfu/mL), with a shelf life of up to 2 years at room temperature, and with a minimum concentration at expiry of $2\times10^{10}$ cfu/mL. The composition includes providing the elements of its formulation, preparation and packaging.

BRIEF DESCRIPTION OF THE FIGURES

FIG. 1 shows *B. japonicum* survival in a highly concentrated liquid inoculant of different compositions and manufacturing processes based on storage time at room temperature (20-25° C.).

FIG. 2 shows *B. japonicum* survival in a highly concentrated liquid inoculant of two compositions according to the type of stabilizer, based on storage time at room temperature (20-25° C.).

FIG. 3 shows *B. japonicum* survival in a highly concentrated liquid inoculant, based on storage time at two temperatures (16 and 20-25° C.).

FIG. 4 shows *B. japonicum* survival in a highly concentrated liquid inoculant, according to the degree of concentration of the bacterial broth culture and the proportion of the stabilizer used in the final formulation, based on storage time at room temperature (20-25° C.).

FIGS. 5-A, 5-B, and 5-C show the number of *Bradyrhizobium* colony forming units (cfu) per seed, when the highly concentrated liquid inoculant is applied after two years of storage.

FIGS. 6-A, 6-B, and 6-C show the number of nodules per plant in primary root, when the highly concentrated liquid inoculant is applied after two years of storage.

FIGS. 7-A, 7-B, and 7-C show the number of nodules per plant in total root, when the highly concentrated liquid inoculant is applied after two years of storage.

FIGS. 8-A, 8-B, and 8-C show the dry mass of nodules per plant in primary root, when the highly concentrated liquid inoculant is applied after two years of storage.

FIGS. 9-A, 9-B, and 9-C show the dry mass of nodules per plant in total root, when the highly concentrated liquid inoculant is applied after two years of storage.

DETAILED DESCRIPTION OF THE INVENTION AND DRAWINGS

Reference is made to the composition of a liquid inoculant highly concentrated in bacteria of the *Bradyrhizobium* genus that nodulate soybean plants, such as: *B. japonicum; B. diazoefficiens; B. elkanii*. The composition adapts to the usual commercial handling of inoculants under the usual storage and transport conditions, and it can reach a shelf life of up to two years and be applied at low doses.

Phase 1—Cellular Multiplication

Firstly, *Bradyrhizobium* bacteria, such as *B. japonicum; B. diazoefficiens; B. elkanii*, are multiplied in an appropriate culture medium such as the widely reported YMB (Yeast-Mannitol-Broth) or its derivations, such as the medium shown in Table 1, which is preferred for the composition of the highly concentrated inoculant to which this invention relates.

TABLE 1

| Modified YMB medium - g/L | |
| --- | --- |
| Glycerol | 25 |
| Yeast Extract | 4 |
| KNO$_3$ | 1.6 |
| MgSO$_4$•7H$_2$O | 0.2 |
| K$_2$HPO$_4$ | 0.5 |
| KH$_2$PO$_4$ | 0.5 |
| (NH$_4$)$_2$HPO$_4$ | 0.4 |
| NaCl | 0.1 |
| MnSO$_4$•H$_2$O | 0.01 |
| FeCl$_3$ | 0.01 |
| Water | 1000 | pH: 6.8-7.0

Bacteria are added to the culture medium, leaving an initial concentration of $1\times10^8$ to $1\times10^9$ cfu/mL, preferably $3\times10^8$ to $7\times10^8$ cfu/mL. Under appropriate temperature and agitation conditions, cellular multiplication suitable for this first stage of processing of the highly concentrated inoculant composition is obtained.

The appropriate incubation temperature ranges between 23 and 30° C., preferably between 27 and 30° C., and the degree of aeration is variable and depends on the element where the cellular multiplication takes place, ranging from Erlenmeyer flasks in an agitation incubator to bio-reactors or automated fermenters. Incubation time can range from 4 to 7 days depending on the bacterial strain considered within the species mentioned in this invention.

At the end of incubation, a level of bacterial concentration between $1.5\times10^{10}$ to $3\times10^{10}$ cfu/mL must be reached. This first stage of bacterial culture development is followed by Phase 2. which includes the process of centrifugation or cell separation from its surrounding medium, with the aim of achieving a highly concentrated bacterial broth ready to continue with the last phase (Phase 3) involving the final formulation process and packaging.

Phase 2—Cellular Concentration

The centrifugation or cell separation process concentrates the amount of bacteria in the bacterial broth from Phase 1. A laboratory centrifuge or an industrial separator can be used for this purpose. For the first case the proper centrifugation speed is between 5000 and 14000 rpm, and speeds between 8000 and 12000 rpm are preferred. Centrifugation time and temperature can vary between 5 and 20 minutes and between 18 and 26° C., respectively, preferably 8 to 15 minutes and 20 to 25° C.

Bacterial broth concentration means that from a normal bacterial broth a bacterial broth concentrated 8 to 20 times is obtained. To use the concentrated broth within the mentioned range, the sediment and part of the supernatant liquid must be used. The sum of the sediment volume and the supernatant volume represents the desired concentration within the mentioned range. The sediment is then vigorously mixed with the remaining supernatant and a homogeneous re-suspension of the highly concentrated bacterial broth is obtained. This material is then ready for final formulation and packaging process (Phase 3), which will result in the highly concentrated inoculant.

Phase 3—Final Formulation

Once the 8× to 20× concentrated bacterial broth is obtained, the final formulation stabilizes the product to achieve a liquid composition with a shelf life of up to 2 years under storage conditions at room temperature of 20-25° C. The parameter defining the shelf life is the bacterial concentration ranging between $10^{10}$ and $10^{11}$ cfu/mL, more specifically between $2\times10^{10}$ and $2\times10^{11}$ cfu/m L, capable of producing optimal nodulation in the soybean crop.

The formulation consists of adding one or more substances mixed with water to the highly concentrated bacterial broth. The substances, dissolved in water, produce "stabilizing" options which can be added to the highly concentrated bacterial broth (Table 2). After the stabilizer is added to the broth, it is exposed to interaction under the same temperature and agitation conditions as in Phase 1.

The stabilizer used must be compatible with the viability of the bacteria and, at the same time, protect the cells from premature deterioration both in the container and on the seed or in the soil.

TABLE 2

| | Substance | | | | | | Substance concentration in |
| --- | --- | --- | --- | --- | --- | --- | --- |
| Stabilizer | Sucrose (g) | Trehalose (g) | CMC (g) | K$_2$HPO$_4$ (g) | KH$_2$PO$_4$ (g) | Water (mL) | the Stabilizer (% weight/weight) |
| A1 | 2000 | 0 | 0 | 5 | 2.5 | 1000 | 66.7 |
| A1810 | 1275 | 0 | 6.3 | 5 | 2.5 | 1000 | 56.3 |
| A2 | 0 | 1000 | 0 | 5 | 2.5 | 1000 | 50.2 |

The stabilizer is incorporated proportionately ranging from 10 to 75% with respect to the volume of the highly concentrated bacterial broth. Preferably, the proportions used range between 20 and 50%.

Once the highly concentrated and stabilizing bacterial broth mixture is obtained, the formulation is subjected to an interaction time called "Process" (P) under the same temperature and agitation conditions as in Phase 1. Processes can vary between 0 and 5 days, preferably 2 to 4 days. The Process may increase the physicochemical assimilation of the stabilizer into the cells and may contribute to improve the stabilization and cell protection qualities of the highly concentrated liquid inoculant.

Once the formulation of the highly concentrated liquid inoculant is complete, it is packaged. The composition can be placed in single- or double-layer low density polyethylene bladders, each layer 35 to 80 µm thick, preferably 50 to 70 µm, using a volume of 0.5 to 15 L, preferably 0.5 to 2 L. This type of packaging allows the gaseous exchange between the composition and the environment, contributing to the metabolic balance of the bacteria and their stabilization during the product's life. In addition, it maintains purity and prevents contamination of particles inside.

The packaged product can be stored at temperatures between 2 to 25° C., although the composition design allows temperatures between 20 to 25° C. while maintaining its useful life for up to 2 years. Given the type of packaging used, no specific relative air humidity is required. There are no specific requirements for brightness either, although it should be preferably stored in the dark.

bacteria on the soybean was measured, the number of bacteria per seed were counted, and the nodulation response in the plant growth chamber was observed, according to the time since the treatment (pre-inoculation).

The highly concentrated liquid inoculant used in this example was manufactured from Stabilizer A1 and contained $1.65 \times 10^{11}$ cfu/mL, with 1.5 year since its manufacture. Prior to application on soybeans, the inoculant (UHC) was mixed with a bacterial protector (Premax LLI). The mixture was let sit for 15 minutes and the proper dose was applied to 200 g of DM 4014 soybean which had been previously treated with commercial agrochemicals. It was also considered a control without agrochemicals. Table 3 shows the products that were used and their application rates on the seeds.

TABLE 3

| Product name | Product type | Active ingredient (%) | Dosage (quantity/kg soybean seed) |
|---|---|---|---|
| UHC | Highly concentrated bacterial inoculant | *Bradyrhizobium japonicum* + *Bradyrhizobium diazoefficiens* (15) | 3 mL (dose1) or 4 mL (dose2) |
| Premax LLI | Bacterial protector | Sugar (% not applicable) | 1 mL |
| Avicta 500 FS | Nematicide and insecticide | Abamectine (50) | 1 mL |
| Cruiser 35 FS | Insecticide | Thiamethoxam (35) | 2 mL |
| Maxim Evolution | Fungicide | Tiabendazole (15) + fludioxonil (2.5) + metalaxyl-M (2) | 1 mL |
| Fluidus 028 | Drying powder | Micas (% not applicable) | 1 g |
| Amulet | Insecticide | Fipronil (20) | 1 mL |
| Cropstar | Insecticide | Imidacloprid (15) + thiodicarb (45) | 6 mL |
| Ritiram Carb Plus | Fungicide | Thiram (35) + carbendazim (15) | 2 mL |
| Standak Top | Fungicide and insecticide | Pyraclostrobin (2.5) + Methyl thiophanate (22.5) + Fipronil (25) | 2 mL |
| Dermacor | Insecticide | Chlorantraniliprole (62.5) | 1 mL |
| Seed + Dry | Nutrition supplement | Ca (4.2) + Mg (1.9) + S (4.2) + Co (0.0012) + Cu (0.08) + Fe (0.9) + Mn (0.25) + Mo (0.0008) + Zn (1) | 2.5 g |

Levels 34, 63 and 78 days after inoculation (dai) were established, which are the times between seed treatment and the biological determinations (early seed treatment or pre-inoculation). The treated seed was stored at two temperatures (20-24° C. and 26° C.) and in darkness.

Technics and Measurements of Results

The number of viable *Bradyrhizobium* per seed was determined using the technique of decimal dilutions and surface dissemination (0.1 mL of inoculum) in Petri dishes containing YMA (Yeast-Mannitol-Agar) medium. In each determination, 50 seeds were shaken for 12 min with 50 mL of purified (demineralized) water sterilized by autoclave, in a 125 mL bottle, at 200 rpm. Three repetitions and 2 dishes by dilution were used. The sown dishes were incubated at 29.5° C. and *Bradyrhizobium* colonies were counted 7 days later.

For the nodulation study, seed was sown in cups with 330 g of sandy soil free of *Bradyrhizobium* (from La Pampa, Argentina, with no soybean crop history). The units were placed in a growth chamber under controlled conditions of temperature (25-28° C.), soil moisture (close to field capacity) and air (60-70% RH), light (8000 lux) and photoperiod (16 h light, 8 h darkness). Irrigation was carried out with purified (demineralized) water sterilized by filtration (0.1

EXAMPLES

Example 1

Survival of *Bradyrhizobium japonicum* on Soybean and Nodulation Response in Treatments with Agrochemicals Used in Brazil The following example shows the results of the use of the highly concentrated inoculant after storage for 1.5 years from its manufacture. The effect of two preservation temperatures of the treated seed was evaluated (20-24° C. and 26° C.). In addition, it was applied with different commercial agrochemicals commonly used in Brazil and its performance was evaluated. The highly concentrated inoculant was applied in 2 different doses and using different application methods. The results were evaluated: the viability of the μm). Two seeds per glass were sown and on the fourth day a thinning of 1 plant per glass was done. We worked with 9 repetitions and 35 days after sowing the plants were processed to determine the 4 nodulation variables: number of nodules per plant (by direct count) in primary and total root; and dry mass of nodules per plant (by weighing nodules dried at 60° C. for 48 hours) in primary and total root.

The response of the treatments can be evaluated according to benchmarks as suitability or agronomic efficiency indicators. One of these benchmarks may be one that meets the minimum acceptable values of two or more of the variables analyzed: *Bradyrhizobium* cfu/seed, ≥5×10$^4$; Number of nodules per plant in primary root ≥2; Number of nodules per plant in total root ≥3; dry mass (mg) of nodules per plant in primary root ≥10; and dry mass (mg) of nodules per plant in total root ≥15. In order to determine suitability or efficiency, the following variables are preferably taken into account: number of nodules per plant in total root and dry mass (mg) of nodules per plant in total root.

Results

Table 4 shows that the highly concentrated (UHC) bacterial inoculant was efficient, as it responded to several cases with ≥3 nodules per plant in total root and ≥15 mg of dry mass of nodules in total root. Suitability was influenced by the degree of compatibility with agrochemicals, seed storage temperature, pre-inoculation time and inoculant dose. A suitable response was achieved of up to 78 days after inoculation (dai) in the presence of different combinations of agrochemicals and seed storage at 20-24° C. The best response under these conditions was observed in seed treatments with "Maxim Evolution+Standak Top//UHC+Premax LLI dose1", "Avicta 500 FS+Cruiser 35 FS+Maxim Evolution//UHC+Premax LLI dose2" and "UHC+Premax LLI dose2/Fluidus 028", which produced ≥6 nodules per plant in total root and ≥32.3 mg of dry mass of nodules in total root.

TABLE 4

| dai | Seed storage temperature (° C.) | Seed treatment | cfu/ seed | No of nodules/ plant in Primary Root | No of nodules/ plant in Total Root | Dry mass (mg) nodules/ plant in Primary Root | Dry mass (mg) nodules/ plant in Total Root |
|---|---|---|---|---|---|---|---|
| 34 | 20-24 | UHC + Premax LLI dose1 | 5.72E+05 | 4.6 | 6.9 | 48.3 | 60.0 |
| 34 | 20-24 | Avicta 500 FS + Cruiser 35 FS + Maxim Evolution // UHC + Premax LLI dose1 | 3.08E+05 | 4.4 | 18.5 | 35.9 | 67.1 |
| 34 | 20-24 | Avicta 500 FS + Cruiser 35 FS + Maxim Evolution // UHC + Premax LLI dose1/Fluidus 028 | 1.97E+05 | 1.6 | 11.3 | 19.6 | 56.6 |
| 34 | 20-24 | Amulet + Cruiser 35 FS + Maxim Evolution // UHC + Premax LLI dose1 | 1.15E+05 | 3.6 | 13.1 | 33.2 | 63.3 |
| 34 | 20-24 | Cropstar // UHC + Premax LLI dose1 | 4.75E+03 | 0.0 | 0.9 | 0.0 | 5.0 |
| 34 | 20-24 | Maxim Evolution + Ritiram Carb Plus // UHC + Premax LLI dose1 | 2.77E+05 | 0.0 | 3.3 | 0.0 | 17.8 |
| 34 | 20-24 | Maxim Evolution + Ritiram Carb Plus // UHC + Premax LLI dose1/Fluidus 028 | 1.95E+05 | 0.0 | 3.3 | 0.0 | 13.8 |
| 34 | 20-24 | Maxim Evolution + Standak Top // UHC + Premax LLI dose1 | 1.04E+06 | 1.4 | 15.6 | 9.8 | 53.4 |
| 34 | 20-24 | Dermacor // UHC + Premax LLI dose1 | 7.77E+05 | 2.1 | 14.1 | 19.9 | 49.0 |
| 34 | 20-24 | UHC + Premax LLI dose1/Fluidus 028 | 4.57E+05 | 1.0 | 14.7 | 10.4 | 49.4 |
| 34 | 20-24 | Standak Top // UHC + Premax LLI dose1 | 3.90E+05 | 2.9 | 9.0 | 27.2 | 48.9 |
| 34 | 20-24 | UHC + Premax LLI dose1/Seed + Dry | 9.17E+04 | 0.8 | 4.2 | 6.8 | 28.3 |
| 34 | 20-24 | UHC + Premax LLI dose2 | 1.79E+06 | 2.3 | 15.9 | 30.6 | 55.0 |
| 34 | 20-24 | Avicta 500 FS + Cruiser 35 FS + Maxim Evolution // UHC + Premax LLI dose2 | 1.05E+06 | 2.7 | 12.1 | 29.2 | 63.2 |
| 34 | 20-24 | Avicta 500 FS + Cruiser 35 FS + Maxim Evolution // UHC + Premax LLI dose2/Fluidus 028 | 6.68E+05 | 3.8 | 11.2 | 26.9 | 55.3 |

TABLE 4-continued

| dai | Seed storage temperature (° C.) | Seed treatment | cfu/ seed | No of nodules/ plant in Primary Root | No of nodules/ plant in Total Root | Dry mass (mg) nodules/ plant in Primary Root | Dry mass (mg) nodules/ plant in Total Root |
| --- | --- | --- | --- | --- | --- | --- | --- |
| 34 | 20-24 | Amulet + Cruiser 35 FS + Maxim Evolution // UHC + Premax LLI dose2 | 7.50E+05 | 4.2 | 15.2 | 37.0 | 71.1 |
| 34 | 20-24 | Cropstar // UHC + Premax LLI dose2 | 9.00E+03 | 0.0 | 1.0 | 0.0 | 10.2 |
| 34 | 20-24 | Maxim Evolution + Ritiram Carb Plus // UHC + Premax LLI dose2 | 1.04E+06 | 0.0 | 3.2 | 0.0 | 22.4 |
| 34 | 20-24 | Maxim Evolution + Ritiram Carb Plus // UHC + Premax LLI dose2/Fluidus 028 | 2.42E+05 | 0.0 | 3.8 | 0.0 | 23.8 |
| 34 | 20-24 | Maxim Evolution + Standak Top // UHC + Premax LLI dose2 | 1.14E+06 | 1.1 | 17.7 | 11.7 | 60.9 |
| 34 | 20-24 | Dermacor // UHC + Premax LLI dose2 | 1.57E+06 | 4.2 | 7.8 | 48.4 | 57.9 |
| 34 | 20-24 | UHC + Premax LLI dose2/Fluidus 028 | 9.87E+05 | 2.2 | 10.2 | 25.2 | 54.8 |
| 34 | 20-24 | Standak Top // UHC + Premax LLI dose2 | 6.18E+05 | 6.4 | 13.8 | 48.0 | 65.2 |
| 34 | 20-24 | UHC + Premax LLI dose2/Seed + Dry | 1.20E+05 | 0.2 | 5.2 | 5.2 | 26.7 |
| 34 | 26 | UHC + Premax LLI dose1 | 3.17E+05 | 3.2 | 13.2 | 39.4 | 54.2 |
| 34 | 26 | Avicta 500 FS + Cruiser 35 FS + Maxim Evolution // UHC + Premax LLI dose1 | 2.67E+05 | 1.8 | 13.9 | 17.4 | 57.6 |
| 34 | 26 | Avicta 500 FS + Cruiser 35 FS + Maxim Evolution // UHC + Premax LLI dose1/Fluidus 028 | 7.60E+04 | 0.8 | 6.2 | 7.0 | 38.0 |
| 34 | 26 | Amulet + Cruiser 35 FS + Maxim Evolution // UHC + Premax LLI dose1 | 1.15E+05 | 0.0 | 6.9 | 0.0 | 46.9 |
| 34 | 26 | Cropstar // UHC + Premax LLI dose1 | 8.33E+03 | 0.0 | 1.0 | 0.0 | 8.1 |
| 34 | 26 | Maxim Evolution + Ritiram Carb Plus // UHC + Premax LLI dose1 | 8.17E+04 | 0.0 | 3.2 | 0.0 | 10.8 |
| 34 | 26 | Maxim Evolution + Ritiram Carb Plus // UHC + Premax LLI dose1/Fluidus 028 | 1.38E+05 | 0.0 | 0.8 | 0.0 | 4.7 |
| 34 | 26 | Maxim Evolution + Standak Top // UHC + Premax LLI dose1 | 1.50E+05 | 0.1 | 10.1 | 0.7 | 49.6 |
| 34 | 26 | Dermacor // UHC + Premax LLI dose1 | 1.28E+05 | 0.4 | 7.6 | 7.3 | 36.7 |
| 34 | 26 | UHC + Premax LLI dose1/Fluidus 028 | 1 24E+05 | 0.6 | 10.9 | 6.8 | 50.8 |
| 34 | 26 | Standak Top // UHC + Premax LLI dose1 | 8.27E+04 | 0.0 | 7.9 | 0.0 | 49.2 |
| 34 | 26 | UHC + Premax LLI dose1/Seed + Dry | 2.08E+04 | 0.0 | 0.9 | 0.0 | 10.2 |
| 34 | 26 | UHC + Premax LLI dose2 | 7.28E+05 | 2.7 | 6.9 | 38.3 | 52.3 |
| 34 | 26 | Avicta 500 FS + Cruiser 35 FS + Maxim Evolution // UHC + Premax LLI dose2 | 1.43E+05 | 0.1 | 8.8 | 1.1 | 49.8 |

TABLE 4-continued

| dai | Seed storage temperature (° C.) | Seed treatment | cfu/ seed | No of nodules/ plant in Primary Root | No of nodules/ plant in Total Root | Dry mass (mg) nodules/ plant in Primary Root | Dry mass (mg) nodules/ plant in Total Root |
|---|---|---|---|---|---|---|---|
| 34 | 26 | Avicta 500 FS + Cruiser 35 FS + Maxim Evolution // UHC + Premax LLI dose2/Fluidus 028 | 1.07E+05 | 0.1 | 5.8 | 1.8 | 41.2 |
| 34 | 26 | Amulet + Cruiser 35 FS + Maxim Evolution // UHC + Premax LLI dose2 | 1.02E+05 | 0.3 | 10.6 | 6.2 | 46.7 |
| 34 | 26 | Cropstar // UHC + Premax LLI dose2 | 6.00E+03 | 0.0 | 0.1 | 0.0 | 1.1 |
| 34 | 26 | Maxim Evolution + Ritiram Carb Plus // UHC + Premax LLI dose2 | 5.38E+04 | 0.0 | 0.6 | 0.0 | 7.1 |
| 34 | 26 | Maxim Evolution + Ritiram Carb Plus // UHC + Premax LLI dose2/Fluidus 028 | 5.40E+04 | 0.0 | 0.4 | 0.0 | 4.9 |
| 34 | 26 | Maxim Evolution + Standak Top // UHC + Premax LLI dose2 | 1.91E+05 | 0.3 | 13.9 | 3.8 | 59.2 |
| 34 | 26 | Dermacor // UHC + Premax LLI dose2 | 1.88E+05 | 1.9 | 9.0 | 18.3 | 45.6 |
| 34 | 26 | UHC + Premax LLI dose2/Fluidus 028 | 3.48E+05 | 1.3 | 6.7 | 20.4 | 48.2 |
| 34 | 26 | Standak Top // UHC + Premax LLI dose2 | 1.17E+05 | 1.1 | 9.1 | 11.3 | 56.0 |
| 34 | 26 | UHC + Premax LLI dose2/Seed + Dry | 4.33E+04 | 0.2 | 2.9 | 3.4 | 16.4 |
| 63 | 20-24 | UHC + Premax LLI dose1 | 7.58E+04 | 1.4 | 10.3 | 18.6 | 35.1 |
| 63 | 20-24 | Avicta 500 FS + Cruiser 35 FS + Maxim Evolution // UHC + Premax LLI dose1 | 3.72E+04 | 0.0 | 11.0 | 0.0 | 51.2 |
| 63 | 20-24 | Avicta 500 FS + Cruiser 35 FS + Maxim Evolution // UHC + Premax LLI dose1/Fluidus 028 | 2.40E+04 | 0.3 | 5.4 | 6.5 | 40.0 |
| 63 | 20-24 | Amulet + Cruiser 35 FS + Maxim Evolution // UHC + Premax LLI dose1 | 8.50E+03 | 0.0 | 7.3 | 0.0 | 40.3 |
| 63 | 20-24 | Cropstar // UHC + Premax LLI dose1 | 3.65E+04 | 0.0 | 0.2 | 0.0 | 1.0 |
| 63 | 20-24 | Maxim Evolution + Ritiram Carb Plus // UHC + Premax LLI dose1 | 1.50E+04 | 0.0 | 0.4 | 0.0 | 2.1 |
| 63 | 20-24 | Maxim Evolution + Ritiram Carb Plus // UHC + Premax LLI dose1/Fluidus 028 | 3.83E+03 | 0.0 | 0.4 | 0.0 | 1.7 |
| 63 | 20-24 | Maxim Evolution + Standak Top // UHC + Premax LLI dose1 | 3.17E+04 | 0.1 | 5.7 | 3.0 | 40.3 |
| 63 | 20-24 | Dermacor // UHC + Premax LLI dose1 | 4.25E+04 | 0.3 | 4.4 | 8.6 | 23.8 |
| 63 | 20-24 | UHC + Premax LLI dose1/Fluidus 028 | 6.50E+04 | 1.0 | 5.8 | 15.7 | 42.3 |
| 63 | 20-24 | Standak Top // UHC + Premax LLI dose1 | 1.00E+04 | 0.0 | 4.4 | 0.0 | 30.6 |
| 63 | 20-24 | UHC + Premax LLI dose1/Seed + Dry | 1.50E+04 | 0.0 | 2.1 | 0.0 | 14.7 |
| 63 | 20-24 | UHC + Premax LLI dose2 | 1.47E+05 | 1.8 | 7.0 | 23.9 | 48.8 |

TABLE 4-continued

| dai | Seed storage temperature (° C.) | Seed treatment | cfu/ seed | No of nodules/ plant in Primary Root | No of nodules/ plant in Total Root | Dry mass (mg) nodules/ plant in Primary Root | Dry mass (mg) nodules/ plant in Total Root |
|---|---|---|---|---|---|---|---|
| 63 | 20-24 | Avicta 500 FS + Cruiser 35 FS + Maxim Evolution // UHC + Premax LLI dose2 | 7.95E+04 | 0.0 | 7.0 | 0.0 | 50.3 |
| 63 | 20-24 | Avicta 500 FS + Cruiser 35 FS + Maxim Evolution // UHC + Premax LLI dose2/Fluidus 028 | 6.83E+04 | 0.0 | 2.9 | 0.0 | 18.2 |
| 63 | 20-24 | Amulet + Cruiser 35 FS + Maxim Evolution // UHC + Premax LLI dose2 | 3.83E+04 | 0.3 | 6.0 | 5.3 | 43.7 |
| 63 | 20-24 | Cropstar // UHC + Premax LLI dose2 | 2.00E+03 | 0.0 | 0.3 | 0.0 | 2.1 |
| 63 | 20-24 | Maxim Evolution + Ritiram Carb Plus // UHC + Premax LLI dose2 | 2.67E+04 | 0.0 | 0.0 | 0.0 | 0.0 |
| 63 | 20-24 | Maxim Evolution + Ritiram Carb Plus // UHC + Premax LLI dose2/Fluidus 028 | 7.50E+03 | 0.9 | 4.9 | 10.6 | 39.4 |
| 63 | 20-24 | Maxim Evolution + Standak Top // UHC + Premax LLI dose2 | 2.00E+04 | 0.2 | 3.6 | 3.4 | 23.7 |
| 63 | 20-24 | Dermacor // UHC + Premax LLI dose2 | 4.50E+04 | 0.0 | 4.8 | 0.0 | 30.0 |
| 63 | 20-24 | UHC + Premax LLI dose2/Fluidus 028 | 1.05E+05 | 0.8 | 2.7 | 11.8 | 24.2 |
| 63 | 20-24 | Standak Top // UHC + Premax LLI dose2 | 4.50E+03 | 0.2 | 6.6 | 3.2 | 43.2 |
| 63 | 20-24 | UHC + Premax LLI dose2/Seed + Dry | 2.33E+04 | 0.0 | 0.7 | 0.0 | 1.8 |
| 63 | 26 | UHC + Premax LLI dose1 | 1.65E+04 | 0.2 | 4.9 | 4.1 | 32.6 |
| 63 | 26 | Avicta 500 FS + Cruiser 35 FS + Maxim Evolution // UHC + Premax LLI dose1 | 3.50E+03 | 0.0 | 4.3 | 0.0 | 26.1 |
| 63 | 26 | Avicta 500 FS + Cruiser 35 FS + Maxim Evolution // UHC + Premax LLI dose1/Fluidus 028 | 1.33E+03 | 0.0 | 1.4 | 0.0 | 9.2 |
| 63 | 26 | Amulet + Cruiser 35 FS + Maxim Evolution // UHC + Premax LLI dose1 | 2.17E+03 | 0.0 | 2.6 | 0.0 | 18.1 |
| 63 | 26 | Cropstar // UHC + Premax LLI dose1 | 1.00E+03 | 0.0 | 0.0 | 0.0 | 0.0 |
| 63 | 26 | Maxim Evolution + Ritiram Carb Plus // UHC + Premax LLI dose1 | 2.25E+03 | 0.0 | 0.0 | 0.0 | 0.0 |
| 63 | 26 | Maxim Evolution + Ritiram Carb Plus // UHC + Premax LLI dose1/Fluidus 028 | 1.00E+03 | 0.0 | 0.4 | 0.0 | 0.3 |
| 63 | 26 | Maxim Evolution + Standak Top // UHC + Premax LLI dose1 | 2.00E+03 | 0.0 | 0.9 | 0.0 | 4.9 |
| 63 | 26 | Dermacor // UHC + Premax LLI dose1 | 1.75E+03 | 0.0 | 1.3 | 0.0 | 9.4 |
| 63 | 26 | UHC + Premax LLI dose1/Fluidus 028 | 1.33E+04 | 0.0 | 4.0 | 0.0 | 17.4 |
| 63 | 26 | Standak Top // UHC + Premax LLI dose1 | 1.00E+03 | 0.0 | 1.4 | 0.0 | 22.6 |
| 63 | 26 | UHC + Premax LLI dose1/Seed + Dry | 2.25E+03 | 0.0 | 0.4 | 0.0 | 2.1 |

TABLE 4-continued

| dai | Seed storage temperature (° C.) | Seed treatment | cfu/ seed | No of nodules/ plant in Primary Root | No of nodules/ plant in Total Root | Dry mass (mg) nodules/ plant in Primary Root | Dry mass (mg) nodules/ plant in Total Root |
| --- | --- | --- | --- | --- | --- | --- | --- |
| 63 | 26 | UHC + Premax LLI dose2 | 2.17E+04 | 1.1 | 6.1 | 23.6 | 45.0 |
| 63 | 26 | Avicta 500 FS + Cruiser 35 FS + Maxim Evolution // UHC + Premax LLI dose2 | 4.00E+03 | 0.1 | 2.2 | 1.9 | 21.7 |
| 63 | 26 | Avicta 500 FS + Cruiser 35 FS + Maxim Evolution // UHC + Premax LLI dose2/Fluidus 028 | 2.67E+03 | 0.0 | 1.2 | 0.0 | 8.4 |
| 63 | 26 | Amulet + Cruiser 35 FS + Maxim Evolution // UHC + Premax LLI dose2 | 3.50E+03 | 0.0 | 1.7 | 0.0 | 10.4 |
| 63 | 26 | Cropstar // UHC + Premax LLI dose2 | 1.00E+03 | 0.0 | 0.1 | 0.0 | 1.1 |
| 63 | 26 | Maxim Evolution + Ritiram Carb Plus // UHC + Premax LLI dose2 | 1.00E+03 | 0.0 | 0.3 | 0.0 | 2.0 |
| 63 | 26 | Maxim Evolution + Ritiram Carb Plus // UHC + Premax LLI dose2/Fluidus 028 | 1.75E+03 | 0.0 | 0.0 | 0.0 | 0.0 |
| 63 | 26 | Maxim Evolution + Standak Top // UHC + Premax LLI dose2 | <1.00E+03 | 0.0 | 2.3 | 0.0 | 14.3 |
| 63 | 26 | Dermacor // UHC + Premax LLI dose2 | 2.50E+03 | 0.0 | 0.7 | 0.0 | 11.6 |
| 63 | 26 | UHC + Premax LLI dose2/Fluidus 028 | 4.28E+04 | 0.0 | 3.8 | 0.0 | 21.6 |
| 63 | 26 | Standak Top // UHC + Premax LLI dose2 | 1.80E+04 | 0.0 | 2.4 | 0.0 | 19.4 |
| 63 | 26 | UHC + Premax LLI dose2/Seed + Dry | 1.35E+04 | 0.0 | 0.8 | 0.0 | 5.1 |
| 78 | 20-24 | UHC + Premax LLI dose1 | 1.62E+04 | 0.0 | 6.0 | 0.0 | 27.1 |
| 78 | 20-24 | Avicta 500 FS + Cruiser 35 FS + Maxim Evolution // UHC + Premax LLI dose1 | 1.03E+04 | 0.0 | 3.9 | 0.0 | 28.1 |
| 78 | 20-24 | Avicta 500 FS + Cruiser 35 FS + Maxim Evolution // UHC + Premax LLI dose1/Fluidus 028 | 4.33E+03 | 0.0 | 0.4 | 0.0 | 6.3 |
| 78 | 20-24 | Amulet + Cruiser 35 FS + Maxim Evolution // UHC + Premax LLI dose1 | 5.67E+03 | 0.1 | 1.1 | 1.6 | 13.4 |
| 78 | 20-24 | Cropstar // UHC + Premax LLI dose1 | <1.00E+03 | 0.0 | 0.4 | 0.0 | 2.9 |
| 78 | 20-24 | Maxim Evolution + Ritiram Carb Plus // UHC + Premax LLI dose1 | 2.00E+03 | 0.0 | 0.5 | 0.0 | 3.8 |
| 78 | 20-24 | Maxim Evolution + Ritiram Carb Plus // UHC + Premax LLI dose1/Fluidus 028 | 2.17E+03 | 0.0 | 0.8 | 0.0 | 3.0 |
| 78 | 20-24 | Maxim Evolution + Standak Top // UHC + Premax LLI dose1 | 6.00E+03 | 2.4 | 6.6 | 19.6 | 32.3 |
| 78 | 20-24 | Dermacor // UHC + Premax LLI dose1 | 5.67E+03 | 1.4 | 3.3 | 4.4 | 8.4 |
| 78 | 20-24 | UHC + Premax LLI dose1/Fluidus 028 | 1.73E+04 | 2.0 | 6.3 | 14.1 | 28.3 |
| 78 | 20-24 | Standak Top // UHC + Premax LLI dose1 | 1.38E+04 | 1.4 | 5.4 | 3.9 | 16.4 |

TABLE 4-continued

| dai | Seed storage temperature (° C.) | Seed treatment | cfu/ seed | No of nodules/ plant in Primary Root | No of nodules/ plant in Total Root | Dry mass (mg) nodules/ plant in Primary Root | Dry mass (mg) nodules/ plant in Total Root |
|---|---|---|---|---|---|---|---|
| 78 | 20-24 | UHC + Premax LLI dose1/Seed + Dry | 2.83E+03 | 0.0 | 0.6 | 0.0 | 1.1 |
| 78 | 20-24 | UHC + Premax LLI dose2 | 5.40E+04 | 2.4 | 8.4 | 23.5 | 41.8 |
| 78 | 20-24 | Avicta 500 FS + Cruiser 35 FS + Maxim Evolution // UHC + Premax LLI dose2 | 1.50E+04 | 1.0 | 6.0 | 7.6 | 32.8 |
| 78 | 20-24 | Avicta 500 FS + Cruiser 35 FS + Maxim Evolution // UHC + Premax LLI dose2/Fluidus 028 | 7.83E+03 | 1.5 | 5.3 | 9.5 | 23.9 |
| 78 | 20-24 | Amulet + Cruiser 35 FS + Maxim Evolution // UHC + Premax LLI dose2 | 1.25E+04 | 1.5 | 3.5 | 15.6 | 24.6 |
| 78 | 20-24 | Cropstar // UHC + Premax LLI dose2 | 1.00E+03 | 0.1 | 0.8 | 6.0 | 9.4 |
| 78 | 20-24 | Maxim Evolution + Ritiram Carb Plus // UHC + Premax LLI dose2 | 3.67E+03 | 0.1 | 0.3 | 0.5 | 0.6 |
| 78 | 20-24 | Maxim Evolution + Ritiram Carb Plus // UHC + Premax LLI dose2/Fluidus 028 | 7.50E+03 | 0.1 | 0.8 | 0.1 | 1.5 |
| 78 | 20-24 | Maxim Evolution + Standak Top // UHC + Premax LLI dose2 | 5.67E+03 | 0.8 | 3.1 | 4.5 | 14.1 |
| 78 | 20-24 | Dermacor // UHC + Premax LLI dose2 | 8.17E+03 | 0.3 | 2.9 | 7.1 | 13.6 |
| 78 | 20-24 | UHC + Premax LLI dose2/Fluidus 028 | 2.17E+04 | 2.0 | 6.1 | 31.0 | 39.4 |
| 78 | 20-24 | Standak Top // UHC + Premax LLI dose2 | 7.50E+03 | 0.4 | 3.3 | 5.6 | 22.6 |
| 78 | 20-24 | UHC + Premax LLI dose2/Seed + Dry | 3.50E+03 | 0.1 | 1.6 | 0.1 | 4.8 |
| 78 | 26 | UHC + Premax LLI dose1 | 4.93E+03 | 0.0 | 1.4 | 0.0 | 7.4 |
| 78 | 26 | Avicta 500 FS + Cruiser 35 FS + Maxim Evolution // UHC + Premax LLI dose1 | 3.17E+02 | 0.0 | 1.8 | 0.0 | 12.4 |
| 78 | 26 | Avicta 500 FS + Cruiser 35 FS + Maxim Evolution // UHC + Premax LLI dose1/Fluidus 028 | 3.00E+02 | 0.0 | 0.1 | 0.0 | 0.8 |
| 78 | 26 | Amulet + Cruiser 35 FS + Maxim Evolution // UHC + Premax LLI dose1 | 1.83E+02 | 0.0 | 0.3 | 0.0 | 5.5 |
| 78 | 26 | Cropstar // UHC + Premax LLI dose1 | <1.00E+02 | 0.0 | 0.1 | 0.0 | 0.8 |
| 78 | 26 | Maxim Evolution + Ritiram Carb Plus // UHC + Premax LLI dose1 | 2.00E+02 | 0.0 | 0.0 | 0.0 | 0.0 |
| 78 | 26 | Maxim Evolution + Ritiram Carb Plus // UHC + Premax LLI dose1/Fluidus 028 | 1.05E+03 | 0.0 | 0.5 | 0.0 | 0.4 |
| 78 | 26 | Maxim Evolution + Standak Top // UHC + Premax LLI dose1 | 2.25E+02 | 0.0 | 0.8 | 0.0 | 3.9 |

TABLE 4-continued

| dai | Seed storage temperature (° C.) | Seed treatment | cfu/ seed | No of nodules/ plant in Primary Root | No of nodules/ plant in Total Root | Dry mass (mg) nodules/ plant in Primary Root | Dry mass (mg) nodules/ plant in Total Root |
|---|---|---|---|---|---|---|---|
| 78 | 26 | Dermacor // UHC + Premax LLI dose1 | 1.95E+03 | 0.0 | 0.1 | 0.0 | 0.5 |
| 78 | 26 | UHC + Premax LLI dose1/Fluidus 028 | 5.67E+02 | 0.3 | 1.1 | 1.8 | 3.8 |
| 78 | 26 | Standak Top // UHC + Premax LLI dose1 | 3.83E+02 | 0.4 | 0.9 | 3.4 | 4.9 |
| 78 | 26 | UHC + Premax LLI dose1/Seed + Dry | 2.17E+02 | 0.0 | 0.1 | 0.0 | 0.1 |
| 78 | 26 | UHC + Premax LLI dose2 | 2.78E+03 | 0.8 | 2.0 | 2.9 | 10.9 |
| 78 | 26 | Avicta 500 FS + Cruiser 35 FS + Maxim Evolution // UHC + Premax LLI dose2 | 1.50E+03 | 0.8 | 2.3 | 11.5 | 18.3 |
| 78 | 26 | Avicta 500 FS + Cruiser 35 FS + Maxim Evolution // UHC + Premax LLI dose2/Fluidus 028 | 3.50E+02 | 0.1 | 1.8 | 0.6 | 5.4 |
| 78 | 26 | Amulet + Cruiser 35 FS + Maxim Evolution // UHC + Premax LLI dose2 | 3.00E+02 | 0.0 | 0.9 | 0.0 | 3.5 |
| 78 | 26 | Cropstar // UHC + Premax LLI dose2 | 1.00E+02 | 0.0 | 0.5 | 0.0 | 1.9 |
| 78 | 26 | Maxim Evolution + Ritiram Carb Plus // UHC + Premax LLI dose2 | 1.00E+02 | 0.0 | 0.3 | 0.0 | 0.1 |
| 78 | 26 | Maxim Evolution + Ritiram Carb Plus // UHC + Premax LLI dose2/Fluidus 028 | 2.00E+02 | 0.0 | 0.8 | 0.0 | 1.8 |
| 78 | 26 | Maxim Evolution + Standak Top // UHC + Premax LLI dose2 | 3.00E+02 | 0.0 | 0.4 | 0.0 | 1.8 |
| 78 | 26 | Dermacor // UHC + Premax LLI dose2 | 1.00E+02 | 0.0 | 0.0 | 0.0 | 0.0 |
| 78 | 26 | UHC + Premax LLI dose2/Fluidus 028 | 1.25E+03 | 0.0 | 0.3 | 0.0 | 0.9 |
| 78 | 26 | Standak Top // UHC + Premax LLI dose2 | <1.00E+02 | 0.4 | 1.0 | 5.4 | 11.0 |
| 78 | 26 | UHC + Premax LLI dose2/Seed + Dry | 2.67E+03 | 0.0 | 0.1 | 0.0 | 0.1 | dai = days after inoculation (pre-inoculation).
"/" = wet sequential method (the first products are applied and then the remaining products are applied onto the wet seed);
"//" = dry sequential method (the first products are applied and after several minutes the remaining products are applied onto the dry seed);
"+" = simultaneous method (the products are mixed and after a few minutes the mixture is applied onto the seed).
UHC + Premax LLI dose1 = 3 mL highly concentrated Inoculant/kg + 1 mL Premax LLI/kg;
UHC + Premax LLI dose2 = 4 mL highly concentrated Inoculant/kg + 1 mL Premax LLI/kg.

Example 2

Survival of *Bradyrhizobium japonicum* on Soybean Seed and Nodulation Response in Treatments with Agrochemicals Used in the United States and Canada This example used the highly concentrated inoculant after 2 years storage since manufacture. In addition, its performance was evaluated in comparison with different commercial agrochemicals commonly used in the United States or Canada. The highly concentrated inoculant was applied in 5 different doses and using different application methods. The results were evaluated according to the viability of the bacteria on the soybean, the number of bacteria per seed; the nodulation response in the plant growth chamber, and the time since treatment (pre-inoculation).

The highly concentrated liquid inoculant used in this example was manufactured from Stabilizer A1 and contained 2, 15×10$^{11}$ cfu/mL, with 2 years since its manufacture. In some seed treatments, the right dose of inoculant (UHC) was directly applied to the seed and in other cases, the inoculant was previously mixed with a bacterial protector (Premax); the mix was let sit for 15 minutes and the proper dose was applied onto the seed. Each seed treatment involved 400 g of DM 3312 variety soybean, recently treated with commercial agrochemicals in widespread use in the United States and/or Canadian markets. Non-agrochemical controls were also considered. Table 5 shows the products used and their application rates on the seeds.

TABLE 5

| Product name | Product type | Active ingredient (%) | Dosage (quantity/kg soybean seed) |
|---|---|---|---|
| UHC | Highly concentrated bacterial inoculant | *Bradyrhizobium japonicum* + *Bradyrhizobium diazoefficiens* (15) | 0.98 mL, 0.73 mL, 0.65 mL, 0.5 mL or 0.48 mL |
| Premax | Bacterial protector | Sugar (% not applicable) | 0.5 mL, 0.25 mL or 0.15 mL |
| Intego Suite Soybeans | Fungicide | Clothianidin (20.06) + ethaboxam (2.97) + ipconazole (0.99) + metalaxyl (0.79) | 2.2 mL |
| CruiserMaxx Vibrance | Insecticide and fungicide | Thiamethoxam (20.8) + mefenoxam (3.13) + fludioxonil (1.04) + sedaxane (1.04) | 2.11 mL |

Levels 34, 77, 120, 149, 181 and 210 days after inoculation (dai) were established, corresponding to the time between the seed treatment and the biological determinations (early seed treatment or pre-inoculation). Storage of the treated seed was in the temperature conditions closest to those in the U.S. and Canadian warehouses, starting with the equivalent of seed treatment in November (fall) (Table 6).

TABLE 6

| Storage temperature of treated seed (° C.) | Storage time of treated seed (dai) |
|---|---|
| 5 | 0 to 30 |
| 2 | 31 to 120 |
| 5 | 121 to 150 |
| 10 | 151 to 180 |
| 16 | 181 to 210 |

The test results were measured in the same way as in the previous example, extensively detailed in the section "Technics and Measurement of Results". The test results can be seen graphically in FIGS. 5-A, 5-B, and 5-C (cfu of *Bradyrhizobium*/seed), FIGS. 6-A, 6-B, and 6-C (nodules per plant in primary root), FIGS. 7-A, 7-B, and 7-C (nodules per plant in total root), FIGS. 8-A, 8-B, and 8-C (dry mass of nodules per plant in primary root) and FIGS. 9-A, 9-B, and 9-C (dry mass of nodules per plant in total root). The highly concentrated bacterial inoculum (UHC) can be verified as effective since it responded in numerous cases with ≥3 nodules per plant in total root and mg of dry mass of nodules in total root. The suitability was influenced by the degree of compatibility with agrochemicals, the pre-inoculation time and the inoculant dose. A suitable response was possible even under the most aggressive conditions for bacteria, given by the 210 dai, the presence of agrochemicals and the lower doses of inoculant (0.48 to 0.65 mL/kg). The best response under these conditions was observed in the following seed treatments: "Intego Suite Soybeans/UHC (0.48 mL/kg)+Premax (0.5 mL/kg)", "Intego Suite Soybeans/UHC (0.65 mL/kg)" and "CruiserMaxx Vibrance/UHC (0.65 mL/kg)", which produced ≥3.9 nodules per plant in total root and ≥15.1 mg of dry mass of nodules in total root.

The invention claimed is:

1. A highly concentrated bacterial liquid inoculant containing
    a concentration of bacteria per volume unit between $10^{10}$ and $10^{11}$ colony forming unit per milliliter (CFU/mL), and
    a stabilizer,
    wherein the stabilizer is a sucrose-based stabilizer, trehalose-based stabilizer, carboxymethyl cellulose (CMS)-based stabilizer, phosphate buffer-based stabilizer or mixtures thereof;
    wherein the inoculant has a shelf life of 2 years at storage temperatures up to 25° C., wherein the minimum concentration at expiry is $2 \times 10^{10}$ CFU/mL.

2. The highly concentrated bacterial liquid inoculant in accordance with claim 1, wherein the bacteria are *Bradyrhizobium diazoefficiens* (*B. diazoefficiens*), *Bradyrhizobium japonicum* (*B. japonicum*) or *Bradyrhizobium elkanii* (*B. elkanii*).

3. The highly concentrated bacterial liquid inoculant in accordance with claim 2, wherein the storage temperature ranges between 2 and 25° C.

4. The highly concentrated bacterial liquid inoculant in accordance with claim 2, wherein the stabilizer is the phosphate buffer-based stabilizer comprising one or more phosphate buffers selected from the group consisting of $K_2HPO_4$ and $KH_2PO_4$.

5. The highly concentrated bacterial liquid inoculant in accordance with claim 4, wherein the stabilizer comprises sucrose, $K_2HPO_4$, and $KH_2PO_4$ having final concentrations of 13 to 33%, 0.033 to 0.083%, and 0.016 to 0.041%, respectively.

6. The highly concentrated bacterial liquid inoculant of claim 4, wherein the stabilizer comprises sucrose from 13 to 33%, trehalose from 10 to 25%, and CMC from 0.05 to 0.14%.

7. The highly concentrated bacterial liquid inoculant of claim 4, wherein the stabilizer comprises 0.033 to 0.083% of $K_2HPO_4$, and 0.016 to 0.041% of $KH_2PO_4$.

8. The highly concentrated bacterial liquid inoculant in accordance with claim 2, wherein the inoculant is for applying onto a seed or in a sowing furrow.

9. The highly concentrated bacterial liquid inoculant in accordance with claim 8, wherein when the inoculant is applied onto a seed or in a sowing furrow, at least one agrochemical product selected from a bacterial protector, a nematicide, an insecticide, a fungicide, a drying powder, and a nutritional supplement, is also applied prior to, after, or simultaneously with the inoculant.

10. The highly concentrated bacterial liquid inoculant in accordance with claim 9, wherein the agrochemical product is applied at a dose of 1 to 6 mL/kg of soybean seed for liquid products or 1 to 2.5 g for dry products.

11. The highly concentrated bacterial liquid inoculant according to claim 9, wherein nematicide is abamectine.

12. The highly concentrated bacterial liquid inoculant according to claim 9, wherein insecticide is selected from the group consisting of: abamectine, thiamethoxam, fipronil, imidacloprid, thiodicarb, thiophanate, chlorantraniliprole and the mixture thereof.

13. The highly concentrated bacterial liquid inoculant according to claim 9, wherein fungicide is selected from the group consisting of: tiabendazole, fludioxonil, metalaxyl, thiram, carbendazim, pyraclostrobin, methyl thiophanate, clothianidin, ethaboxam, ipconazole, mefenoxam, sedaxane and the mixture thereof.

14. The highly concentrated bacterial liquid inoculant in accordance with claim 1, wherein the storage temperature ranges between 2 and 25° C.

15. The highly concentrated bacterial liquid inoculant in accordance with claim 14, wherein the inoculant is for applying onto a seed or in a sowing furrow.

16. The highly concentrated bacterial liquid inoculant in accordance with claim 15, wherein when the inoculant is applied onto a seed or in a sowing furrow, at least one agrochemical product selected from a bacterial protector, a nematicide, an insecticide, a fungicide, a drying powder, and a nutritional supplement, is also applied prior to, after, or simultaneously with the inoculant.

17. The highly concentrated bacterial liquid inoculant in accordance with claim 16, wherein the agrochemical product is applied at a dose of 1 to 6 mL/kg of soybean seed for liquid products or 1 to 2.5 g for dry products.

18. The highly concentrated bacterial liquid inoculant according to claim 16, wherein nematicide is abamectine.

19. The highly concentrated bacterial liquid inoculant according to claim 16, wherein insecticide is selected from the group consisting of: abamectine, thiamethoxam, fipronil, imidacloprid, thiodicarb, thiophanate, chlorantraniliprole and the mixture thereof.

20. The highly concentrated bacterial liquid inoculant according to claim 16, wherein fungicide is selected from the group consisting of: tiabendazole, fludioxonil, metalaxyl, thiram, carbendazim, pyraclostrobin, methyl thiophanate, clothianidin, ethaboxam, ipconazole, mefenoxam, sedaxane and the mixture thereof.

21. The highly concentrated bacterial liquid inoculant in accordance with claim 1, wherein the stabilizer is the phosphate buffer-based stabilizer comprising one or more phosphate buffers selected from the group consisting of $K_2HPO_4$ and $KH_2PO_4$, wherein said buffers are present in an effective amount to prevent pH variation of the inoculant.

22. The highly concentrated bacterial liquid inoculant in accordance with claim 21, wherein the inoculant is for applying onto a seed or in a sowing furrow.

23. The highly concentrated bacterial liquid inoculant in accordance with claim 22, wherein when the inoculant is applied onto a seed or in a sowing furrow, at least one agrochemical product selected from a bacterial protector, a nematicide, an insecticide, a fungicide, a drying powder, and a nutritional supplement, is also applied prior to, after, or simultaneously with the inoculant.

24. The highly concentrated bacterial liquid inoculant in accordance with claim 23, wherein the agrochemical product is applied at a dose of 1 to 6 mL/kg of soybean seed for liquid products or 1 to 2.5 g for dry products.

25. The highly concentrated bacterial liquid inoculant according to claim 23, wherein nematicide is abamectine.

26. The highly concentrated bacterial liquid inoculant according to claim 23, wherein insecticide is selected from the group consisting of: abamectine, thiamethoxam, fipronil, imidacloprid, thiodicarb, thiophanate, chlorantraniliprole and the mixture thereof.

27. The highly concentrated bacterial liquid inoculant according to claim 23, wherein fungicide is selected from the group consisting of: tiabendazole, fludioxonil, metalaxyl, thiram, carbendazim, pyraclostrobin, methyl thiophanate, clothianidin, ethaboxam, ipconazole, mefenoxam, sedaxane and the mixture thereof.

28. The highly concentrated bacterial liquid inoculant in accordance with claim 1, wherein the stabilizer is the sucrose-based stabilizer having a final concentration of 13 to 33% of sucrose.

29. The highly concentrated bacterial liquid inoculant in accordance with claim 1, wherein the inoculant is for applying onto a seed or in a sowing furrow.

30. The highly concentrated bacterial liquid inoculant in accordance with claim 29, wherein when the inoculant is applied onto a seed or in a sowing furrow, at least one agrochemical product selected from a bacterial protector, a nematicide, an insecticide, a fungicide, a drying powder, and a nutritional supplement, is also applied prior to, after, or simultaneously with the inoculant.

31. The highly concentrated bacterial liquid inoculant in accordance with claim 30, wherein the agrochemical product is applied at a dose of 1 to 6 mL/kg of soybean seed for liquid products or 1 to 2.5 g for dry products.

32. The highly concentrated bacterial liquid inoculant according to claim 31, wherein nematicide is abamectine.

33. The highly concentrated bacterial liquid inoculant according to claim 31, wherein insecticide is selected from the group consisting of: abamectine, thiamethoxam, fipronil, imidacloprid, thiodicarb, thiophanate, chlorantraniliprole and the mixture thereof.

34. The highly concentrated bacterial liquid inoculant according to claim 31, wherein fungicide is selected from the group consisting of: tiabendazole, fludioxonil, metalaxyl, thiram, carbendazim, pyraclostrobin, methyl thiophanate, clothianidin, ethaboxam, ipconazole, mefenoxam, sedaxane and the mixture thereof.

35. The highly concentrated bacterial liquid inoculant according to claim 30, wherein nematicide is abamectine.

36. The highly concentrated bacterial liquid inoculant according to claim 30, wherein insecticide is selected from the group consisting of: abamectine, thiamethoxam, fipronil, imidacloprid, thiodicarb, thiophanate, chlorantraniliprole and the mixture thereof.

37. The highly concentrated bacterial liquid inoculant according to claim 30, wherein fungicide is selected from the group consisting of: tiabendazole, fludioxonil, metalaxyl, thiram, carbendazim, pyraclostrobin, methyl thiophanate, clothianidin, ethaboxam, ipconazole, mefenoxam, sedaxane and the mixture thereof.

38. The highly concentrated bacterial liquid inoculant of claim 1, wherein the stabilizer comprises sucrose from 13 to 33%, trehalose from 10 to 25%, and CMC from 0.05 to 0.14%.

39. The highly concentrated bacterial liquid inoculant of claim 1, wherein the stabilizer comprises 0.033 to 0.083% of $K_2HPO_4$, and 0.016 to 0.041% of $KH_2PO_4$.

\* \* \* \* \*